(12) United States Patent
Lee et al.

(10) Patent No.: US 11,596,595 B2
(45) Date of Patent: *Mar. 7, 2023

(54) INTRAVESICAL DRUG DELIVERY DEVICE WITH RETENTION FRAME AND DRUG TABLETS

(71) Applicant: TARIS Biomedical LLC, Lexington, MA (US)

(72) Inventors: Heejin Lee, Bedford, MA (US); Cheryl Larrivee-Elkins, Framingham, MA (US)

(73) Assignee: TARIS Biomedical LLC, Lexington, MA (US)

( * ) Notice: Subject to any disclaimer, the term of this patent is extended or adjusted under 35 U.S.C. 154(b) by 392 days.

This patent is subject to a terminal disclaimer.

(21) Appl. No.: 16/715,048

(22) Filed: Dec. 16, 2019

(65) Prior Publication Data

US 2020/0113817 A1  Apr. 16, 2020

Related U.S. Application Data

(63) Continuation of application No. 12/825,215, filed on Jun. 28, 2010, now Pat. No. 10,543,166.

(Continued)

(51) Int. Cl.
*A61K 9/00* (2006.01)
*A61K 9/20* (2006.01)
(Continued)

(52) U.S. Cl.
CPC .......... *A61K 9/0004* (2013.01); *A61K 9/0034* (2013.01); *A61K 9/2027* (2013.01); *A61K 9/2031* (2013.01); *A61K 9/2072* (2013.01); *A61K 9/2095* (2013.01); *A61K 31/165* (2013.01); *A61K 31/167* (2013.01);
(Continued)

(58) Field of Classification Search
CPC .. A61K 9/0004; A61K 9/0034; A61K 9/2072; A61M 31/002
See application file for complete search history.

(56) References Cited

U.S. PATENT DOCUMENTS 3,089,815 A  5/1963  Lieb et al.
3,854,480 A  12/1974  Zaffaroni
(Continued)

FOREIGN PATENT DOCUMENTS

DE  3332156 A1  3/1985
EP  0572932 A2  12/1993
(Continued)

OTHER PUBLICATIONS

Ali, et al., "Lidocaine As Endotracheal Tube Cuff Inflating Agent," JAFMC Bangladesh, vol. 5, No. 1 (Jun. 2009), pp. 25-28.
(Continued)

*Primary Examiner* — Bradley J Osinski
(74) *Attorney, Agent, or Firm* — Eversheds Sutherland (US) LLP

(57) ABSTRACT

Intravesical drug delivery devices that include a device body, a number of solid drug tablets, and a retention frame. The device body includes a drug reservoir lumen and a retention frame lumen. The drug tablets is positioned in the drug reservoir lumen, and the retention frame is positioned in the retention frame lumen.

21 Claims, 8 Drawing Sheets

Related U.S. Application Data

(60) Provisional application No. 61/241,382, filed on Sep. 10, 2009, provisional application No. 61/220,865, filed on Jun. 26, 2009.

(51) Int. Cl.
  *A61K 31/167* (2006.01)
  *A61M 31/00* (2006.01)
  *A61K 31/165* (2006.01)
  *B65B 1/16* (2006.01)
  *A61K 31/16* (2006.01)

(52) U.S. Cl.
  CPC ........ *A61M 31/002* (2013.01); *A61M 31/007* (2013.01); *B65B 1/16* (2013.01); *A61K 9/2004* (2013.01); *A61K 31/16* (2013.01); *A61M 2202/06* (2013.01)

(56) References Cited

U.S. PATENT DOCUMENTS

| | | |
|---|---|---|
| 3,901,232 A | 8/1975 | Michaels et al. |
| 3,888,975 A | 12/1975 | Ramwell |
| 3,935,860 A | 2/1976 | Hoff |
| 4,016,251 A | 4/1977 | Higuchi et al. |
| 4,210,670 A | 7/1980 | Cooke |
| 4,235,236 A | 11/1980 | Theeuwes |
| 4,326,522 A | 4/1982 | Guerrero et al. |
| 4,392,848 A | 7/1983 | Lucas et al. |
| 4,449,980 A | 5/1984 | Millar et al. |
| 4,475,916 A | 10/1984 | Himmelstein |
| 4,578,263 A | 3/1986 | Whitehead |
| 4,629,449 A | 12/1986 | Wong |
| 4,655,219 A | 4/1987 | Petruzzi |
| 4,678,463 A | 7/1987 | Millar |
| 4,731,054 A | 3/1988 | Billeter et al. |
| 4,797,287 A | 1/1989 | Pich et al. |
| 4,814,183 A | 3/1989 | Zentner |
| 4,871,542 A | 10/1989 | Vilhardt |
| 4,968,507 A | 11/1990 | Zentner et al. |
| 4,973,304 A | 11/1990 | Graham et al. |
| 5,366,738 A | 11/1994 | Rork et al. |
| 5,441,550 A | 8/1995 | Hassenboehler, Jr. et al. |
| 5,499,997 A | 3/1996 | Sharpe et al. |
| 5,516,522 A | 5/1996 | Peyman et al. |
| 5,551,954 A | 9/1996 | Buscemi et al. |
| 5,709,874 A | 1/1998 | Hanson et al. |
| 5,788,980 A | 8/1998 | Nabahi |
| 5,795,591 A | 8/1998 | Lee et al. |
| 5,830,230 A | 11/1998 | Berryman et al. |
| 5,851,217 A | 12/1998 | Wolff et al. |
| 5,855,906 A | 1/1999 | McClay |
| 5,869,081 A | 2/1999 | Jackanicz et al. |
| 5,972,372 A | 10/1999 | Saleh et al. |
| 5,989,581 A | 11/1999 | Groenewegen |
| 6,039,967 A | 3/2000 | Ottoboni et al. |
| 6,039,968 A | 3/2000 | Nabahi |
| 6,083,933 A | 7/2000 | Hahn |
| 6,086,909 A | 7/2000 | Harrison et al. |
| 6,139,535 A | 10/2000 | Greelis et al. |
| 6,171,298 B1 | 1/2001 | Matsuura et al. |
| 6,293,923 B1 | 9/2001 | Yachia et al. |
| 6,398,718 B1 | 6/2002 | Yachia et al. |
| 6,416,780 B1 | 7/2002 | Passmore et al. |
| 6,444,224 B1 | 9/2002 | Rathbone et al. |
| 6,464,999 B1 | 10/2002 | Huo et al. |
| 6,482,837 B1 | 11/2002 | Wood |
| 6,524,608 B2 | 2/2003 | Ottoboni et al. |
| 6,537,193 B1 | 3/2003 | Lennox |
| 6,649,186 B1* | 11/2003 | Robinson ............. A61K 9/1694 424/466 |
| 6,712,784 B2 | 3/2004 | Huang |
| 6,749,617 B1 | 6/2004 | Palasis et al. |
| 6,753,011 B2 | 6/2004 | Faour |
| 6,899,890 B2 | 5/2005 | Kirschner et al. |
| 6,951,654 B2 | 10/2005 | Malcom et al. |
| 6,976,950 B2 | 12/2005 | Connors et al. |
| 7,005,138 B2 | 2/2006 | Mahashabde et al. |
| 7,232,421 B1 | 6/2007 | Gambale et al. |
| 7,521,064 B2 | 4/2009 | Saxena et al. |
| 7,647,112 B2 | 1/2010 | Tracey et al. |
| 2003/0017198 A1 | 1/2003 | Yeh et al. |
| 2003/0118649 A1 | 6/2003 | Gao et al. |
| 2003/0118692 A1 | 6/2003 | Wang et al. |
| 2003/0139800 A1 | 7/2003 | Campbell |
| 2003/0143268 A1 | 7/2003 | Lewis et al. |
| 2004/0022824 A1 | 2/2004 | Li et al. |
| 2004/0149294 A1 | 8/2004 | Gianchandani et al. |
| 2004/0220552 A1 | 11/2004 | Heruth et al. |
| 2004/0260027 A1 | 12/2004 | Friedman et al. |
| 2004/0260272 A1 | 12/2004 | Friedman et al. |
| 2005/0192210 A1 | 9/2005 | Rothbard et al. |
| 2005/0228482 A1 | 10/2005 | Herzog et al. |
| 2005/0234013 A1 | 10/2005 | Parsons |
| 2005/0234431 A1 | 10/2005 | Williams et al. |
| 2005/0238733 A1 | 10/2005 | Henry |
| 2006/0105010 A1 | 5/2006 | Rahe et al. |
| 2006/0122689 A1 | 6/2006 | Kocur et al. |
| 2006/0234978 A1 | 10/2006 | Marcum |
| 2006/0259118 A1 | 11/2006 | Pal et al. |
| 2006/0264897 A1 | 11/2006 | Lobl et al. |
| 2006/0264912 A1 | 11/2006 | Mcintyre et al. |
| 2007/0172507 A1 | 7/2007 | Zupkas et al. |
| 2007/0172508 A1 | 7/2007 | Zupkas et al. |
| 2007/0202151 A1 | 8/2007 | Lee et al. |
| 2007/0254014 A1 | 11/2007 | Ahmed et al. |
| 2008/0044450 A1 | 2/2008 | Brandon et al. |
| 2008/0051740 A1 | 2/2008 | Sokal et al. |
| 2008/0111269 A1 | 5/2008 | Politi et al. |
| 2009/0004246 A1 | 1/2009 | Woolfson et al. |
| 2009/0149833 A1* | 6/2009 | Cima ................... A61K 9/0034 604/517 |
| 2009/0317465 A1 | 12/2009 | Peppas |
| 2010/0003297 A1 | 1/2010 | Tobias et al. |
| 2010/0076261 A1 | 3/2010 | Neeman et al. |
| 2010/0330149 A1 | 12/2010 | Lee et al. |
| 2011/0060309 A1 | 3/2011 | Lee et al. |

FOREIGN PATENT DOCUMENTS

| | | |
|---|---|---|
| JP | 10-298107 A | 11/1988 |
| JP | 2005036004 A | 2/2005 |
| WO | 1998/31415 A1 | 2/1998 |
| WO | 1999/18884 A1 | 4/1999 |
| WO | 2000/040234 A1 | 7/2000 |
| WO | 2001/067991 A1 | 9/2001 |
| WO | 2002/085428 A2 | 10/2002 |
| WO | 2003/009882 A2 | 2/2003 |
| WO | 2004/037318 A2 | 5/2004 |
| WO | 2005/072751 A1 | 8/2005 |
| WO | 2005/115245 A1 | 12/2005 |
| WO | 2006/121969 A1 | 11/2006 |
| WO | 2007/021964 A2 | 2/2007 |
| WO | 2007/115259 A2 | 10/2007 |
| WO | 2008/038281 A2 | 4/2008 |
| WO | 2008/051889 A1 | 5/2008 |
| WO | 2008/115536 A2 | 9/2008 |
| WO | 2009/029958 A1 | 3/2009 |

OTHER PUBLICATIONS

Amark, et al., "Follow-Up of Long-Time Treatment with Intravesical Oxybutynin for Neurogenic Bladder in Children," European Urology, vol. 34 (1998), pp. 148-153.

Au, et al., "Methods to Improve Efficacy of Inliavesical Mitomycin C: Results of a Randomized Phase III Trial," Journal of the National Cancer Institute, vol. 93, No. 8 (Apr. 18, 2001), pp. 597-604.

Beiko, et al., "Urinary Tract Biomaterials," The Journal of Urology, vol. 171 (Jun. 2004), pp. 2438-2444.

Birch, et al., "Absorption Characteristics of Lignocaine Following Intravesical Instillation," Scand J Urol Nephrol, vol. 28 (1994), pp. 359-364.

(56) References Cited

OTHER PUBLICATIONS

Burmeister, et al., "Intravescia instillation of trospium chloride, oxybutynin and verapamil for relaxation of the bladder detrusor muscle. A placebo controlled, randomized clinical test," Arzneimittelforschung., vol. 48, No. 5 (May 1998), pp. 486-491. Abstract.
Fraser, et al., "The Future of Bladder Control—Intravesical Drug Delivery, a Pinch of Pepper, and Gene Therapy," Reviews in Urology, vol. 4, No. 1 (2002).
Gasion, et al., "Improving Efficacy of Intravesical Chemotherapy," European Urology, vol. 50 (2006), pp. 225-234, Elsevier B.V.
Giannantoni, et al., "New Frontiers in Intravesical Therapies and Drug Delivery," European Urology, vol. 50 (2006), pp. 1183-1193, Elsevier B.V.
Grayson, et al., Molecular release from a polymeric microreservoir device: Influence of chemistry, polymer swelling, and loading on device performance, J Biomed Mat Res, vol. 69A, No. 3 (2004), pp. 502-512.
Henry, et al., "Topical Anesthesia of the Bladder," Abstracts, A61.
Highley, et al., "Intravesical Drug Delivery Pharmacokinetic and Clinical Considerations," Clinical Pharmacokinetic, vol. 37, No. 1 (Jul. 1999), pp. 59-73, Adis International Limited.
Li, et al., "Water Based Silicone Elastomer Controlled Release Tablet Film Coating III—Drug Release Mechanisms," Drug Development and Industrial Pharmacy, vol. 15, No. 12 (1989), pp. 1943-1968, Marcel Dekker, Inc.
Malmstrom, Per-Uno, "Intravesical therapy of superficial bladder cancer," Critical Reviews in Oncology Hematology, vol. 47 (2003), pp. 109-126, Elsevier Science.
Santus, et al., "Osmotic drug delivery: a review of the patent literature," Journal of Controlled Release, vol. 35 (1995), pp. 1-21.
Tyagi, et al., "Local Drug Delivery to Bladder Using Technology Innovations," Urological Clinics of North America, vol. 33 (2006), pp. 519-530, Elsevier Inc.
Walker, et al., "Intravesical Chemotherapy: In Vitro Studies on the Relationship Between Dose and Cytotoxicity," Urological Research, vol. 14 (1986), pp. 137-140, Springer-Veriag.
Woolfson, et al., "Design of a silicone reservoir intravaginal ring for the delivery of oxybutynin," Journal of Controlled Release, vol. 91 (2003), pp. 465-476, Elsevier B.V.
Wright, et al., "Implantable Technology," Drug Delivery Technologies, pp. 1-15 (http://www.drugdeliverytech.com/cgi-bin/articles.cgi?idArticle=115), Accessed Aug. 8, 2006.
Wright, et al., Pumps/Osmotic, Encyclopedia of Controlled Drug Delivery, vol. 2 (1999), pp. 896-920, New York; John Wiley.
International Search Report and Written Opinion for PCT/US2010/040251, dated Oct. 8, 2010.

* cited by examiner

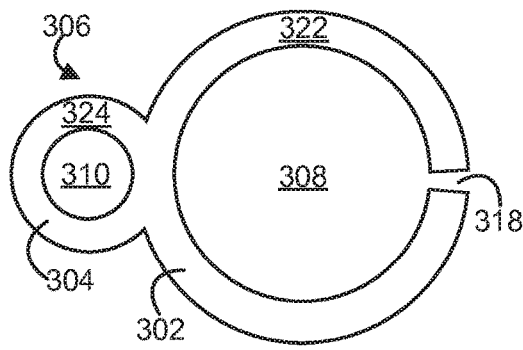
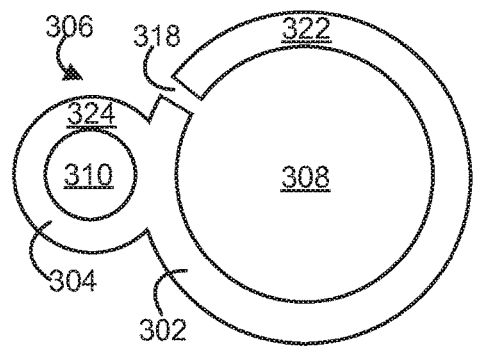
FIG. 5A  FIG. 5B
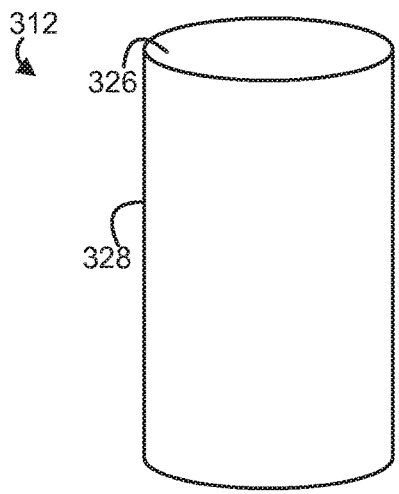
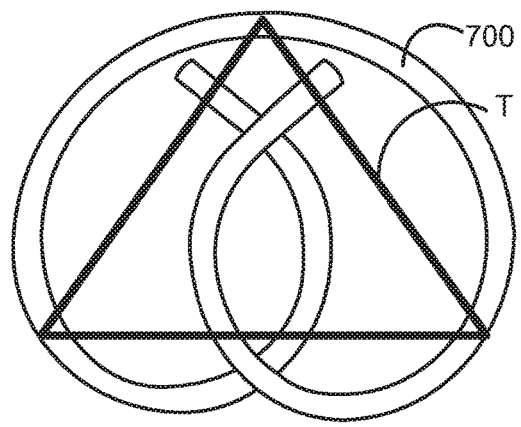
FIG. 6  FIG. 7
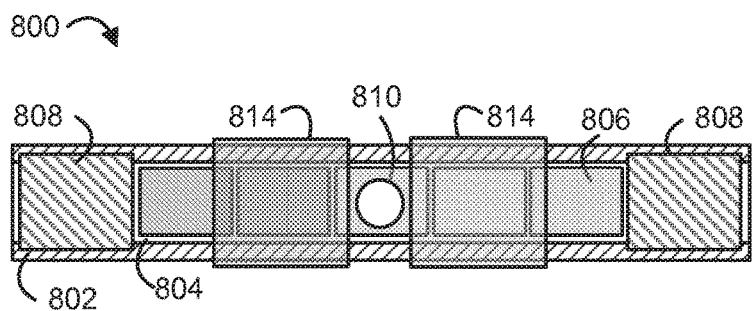
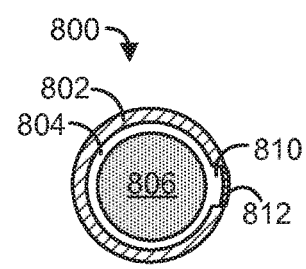
FIG. 8A  FIG. 8B

INTRAVESICAL DRUG DELIVERY DEVICE WITH RETENTION FRAME AND DRUG TABLETS

CROSS-REFERENCE TO RELATED APPLICATIONS

The present application is a continuation of U.S. patent application Ser. No. 12/825,215, filed Jun. 28, 2010, which claims priority to U.S. Provisional Patent Application No. 61/220,865, filed Jun. 26, 2009, and U.S. Provisional Patent Application No. 61/241,382, filed Sep. 10, 2009, each of which is incorporated by reference herein.

BACKGROUND

This disclosure is generally in the field of controlled drug delivery, and more particularly in the field of implantable medical devices for controlled drug release and drug formulations for use with implantable medical devices.

A variety of devices and methods have been developed to deliver drug locally or regionally to mitigate problems associated with systemic drug delivery. Local delivery of drug to some tissue sites could be improved, however, particularly with respect to extended drug delivery from devices that are less invasive and uncomfortable for the patient.

Some treatments could be improved by implanting a drug delivery device in a body lumen or cavity such as the bladder. For example, interstitial cystitis (IC), painful bladder syndrome (PBS), and chronic prostatitis/chronic pelvic pain syndrome (CP/CPPS) are chronic painful disorders that are often treated by delivering a lidocaine solution to the bladder via instillation, but the frequent instillations required for sustained relief entail inconvenience, discomfort, and the risk of infection associated with urinary catheterization. Similarly, the symptoms of neurogenic bladder may be treated by delivering drugs to the bladder via intermittent catheterization, which carries the drawbacks described above, among others. These and other therapeutic or prophylactic treatments, including those for acute post-operative pain, could benefit from drug delivery devices for implantation in the bladder, particularly where local or regional drug delivery is sought, such as when the side effects of systemic drug delivery are intolerable or when bioavailability from oral administration is too low.

Implantable drug delivery devices for the bladder are known but suffer from one or more deficiencies. Some such known devices are loaded with a drug solution, which are capable only of carrying and releasing a relatively smaller amount of drug than what could be delivered in a less voluminous form, such as without a solvent or carrying fluid for the drug. An example is the UROS infuser device by Situs Corporation, as disclosed in U.S. Pat. Nos. 6,171,298, 6,183,461, and 6,139,535, which can deliver pharmaceutical solutions of, for example, oxybutynin for the treatment of overactive bladder or mitomycin C for the treatment of bladder cancer. It would be desirable to provide drug delivery systems and devices that provide higher ratios of drug volume:device volume.

Conventional solid dosage forms are primarily designed for oral administration and systemic delivery, not local delivery to the bladder. Solid drug forms may not be suited for loading into implantable devices, particularly tiny devices of millimeter or micrometer scales, such as in a manner that is consistent and repeatable. Furthermore, these solid dosage forms are not designed to be sterilized or to be provided in sterile packaging.

Accordingly, a need exists for an improved implantable drug delivery device, for example, that is sufficiently small to reduce discomfort and pain associated with deployment and retention, that can reduce the number of surgical or interventional procedures required for implantation and delivery of drug over the treatment period, that can provide controlled delivery over an extended period, that can carry an effective amount of drug for the extended period in a sufficiently small payload volume, and that can be retained in the bladder or other vesicle or lumen without excretion or elimination until the drug payload is at least substantially released, even when the drug is delivered over a period of days or weeks.

SUMMARY

In one aspect, a drug delivery device is provided that includes a device body, a number of solid, compressed drug tablets, and a retention frame. The device body includes a drug reservoir lumen and a retention frame lumen. The number of solid, compressed drug tablets is positioned in the drug reservoir lumen, and the retention frame is positioned in the retention frame lumen. An interstice between any two adjacent drug tablets facilitates deformation of the device body. The drug tablets may be mini-tablets aligned in the drug reservoir lumen.

In certain embodiments, the drug tablets include lidocaine hydrochloride or lidocaine base in tablet form.

The device body may include a drug reservoir tube and a retention frame tube. The drug reservoir tube may define the drug reservoir lumen, and the retention frame tube may define the retention frame lumen. The retention frame tube may be longitudinally aligned and coupled to the drug reservoir tube. In such embodiments, the drug reservoir tube and the retention frame tube may be formed together by an extrusion process or a molding process. The two tubes may include a water permeable silicone. The device body may include an aperture in fluid communication with the drug reservoir lumen. The retention frame may be configured to spontaneously assume a coiled shape. The retention frame may include an elastic wire.

In another aspect, a method is provided for loading a drug delivery device. The method may include positioning one or more solid drug units upstream of the drug delivery device and driving the drug units into the drug delivery device with a flow of pressurized gas. The drug delivery device may include an elastic tube. Positioning one or more drug units upstream of the drug delivery device may further include orienting the drug units to enter the drug delivery device and/or aligning the drug units in a row adjacent to an entry into the drug delivery device. Driving the drug units into the drug delivery device with a flow of pressurized gas may include one or more of directing a positive pressure gas flow toward an entry of the drug delivery device, depressing a syringe filled with air, operating a vacuum associated with an exit of the drug delivery device, and blocking at least one orifice of the drug delivery device to impede the flow of pressurized gas from escaping.

The method may further include one or more of stopping the drug units from exiting the drug delivery device, permitting the flow of pressurized gas to travel about outer peripheries of the drug units, filtering the flow of pressurized gas before the gas enters the drug delivery device to remove contaminants, and filtering the flow of pressurized gas after the gas exits the drug delivery device to remove at least a portion of any drug particles and/or excipient particles entrained in the pressurized gas.

In another aspect, a system is provided for loading a drug delivery device. The system may include an entry channel, a drug unit source, and a pressurized gas source. The entry channel is in communication with the drug delivery device and includes a drug entry opening. A drug unit source is in communication with the entry channel via the drug entry opening. The pressurized gas source is in communication with the entry channel from a location upstream of the drug entry opening. The pressurized gas source is operable to direct a flow of pressurized gas through the entry channel.

The system may further include a drug unit source valve, a pressurized gas valve, and a controller. The drug unit source valve may be operable to selectively permit or prevent drug units from passing through the drug entry opening. The pressurized gas source valve may be operable to selectively permit or prevent the flow of pressurized gas from passing through the entry channel. The controller may be operable to control the drug unit source valve and the pressurized gas source valve.

BRIEF DESCRIPTION OF THE DRAWINGS

FIGS. 5A and 5B illustrate cross-sectional views of a device body of the drug delivery device shown in FIG. 3, with FIGS. 5A and 5B illustrating various placements of an aperture.

FIG. 6 is a perspective view of an embodiment of a solid drug tablet for implantation or intravesical insertion.

FIG. 7 is an illustration showing the size of an example drug delivery device in comparison to an approximation of the bladder trigone region.

FIGS. 8A and 8B illustrate an embodiment of a drug reservoir portion, wherein FIG. 8A is a plan view and FIG. 8B is a side cross-sectional view.

DETAILED DESCRIPTION

Figure 1:
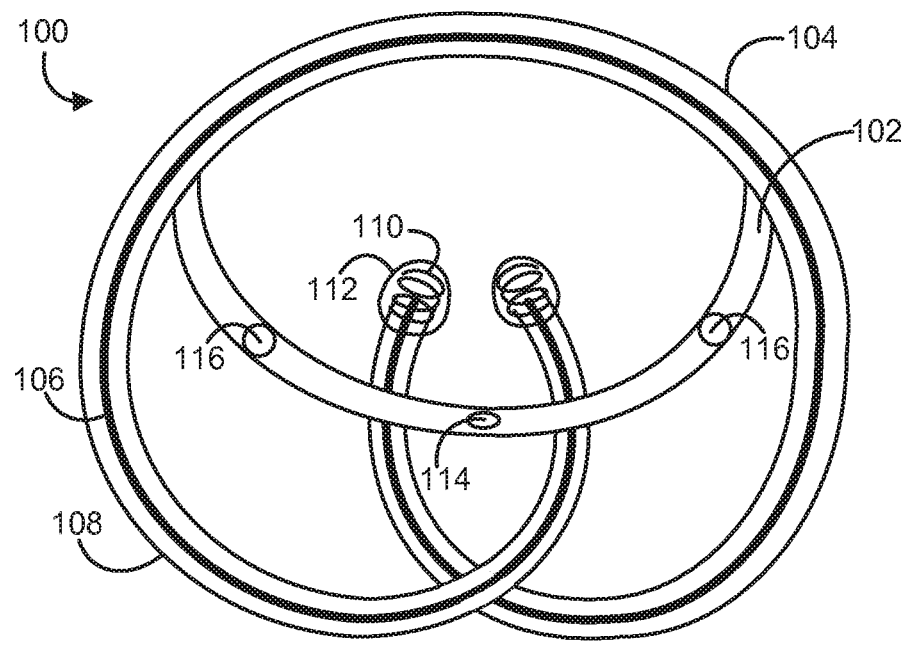
FIG. 1 is a plan view of an embodiment of a drug delivery device.

Implantable devices are provided that can be deployed, or implanted, into a lumen or body cavity of a patient, such as the bladder or another genitourinary site, for release of one or more drugs over an extended period. Drug forms for use with such devices are also disclosed, along with systems and methods of making such drug forms and systems and methods of loading such drug forms into the implantable devices. The devices, methods, and drug forms described herein improve upon those described in U.S. Publication No. 2009/0149833, published Jun. 11, 2009, which is incorporated herein by reference.

The implantable device is designed for deployment into and retention within a portion of the body, such as the bladder. The device may be flexible so that the device can be deformed for insertion, yet once implanted the device may resist excretion in response to the forces of urination or other forces. In particular embodiments, an implantable drug delivery device is loaded with one or more drugs in the form of a number of solid drug units, such as tablets or pellets. Using solid drug formulations permits (i) reducing the size of an implantable device that delivers a selected payload (e.g., mass of drug) or (ii) increasing the payload that may be delivered from a device of a selected size, or (iii) a combination thereof.

Advantageously, the drug loaded device in a preferred embodiment is flexible or deformable despite being loaded with solid drug, as each drug unit may be permitted to move with reference to adjacent drug units. In particular, interstices or breaks between the individual drug units may form reliefs that permit deformation of the device, while allowing the individual drug units to retain their solid form. In one embodiment, the solid drug is loaded in the drug delivery device by positioning one or more drug units near an entry into the drug delivery device and driving the drug units into the drug delivery device using a pressurized gas source, such as by depressing a syringe of air in fluid communication with the device. For example, the drugs may be serially aligned in the narrow, elongated lumen of a drug reservoir.

In particular embodiments, the drug delivery device is small, such as small enough to be inserted through a deployment instrument extending through the urethra into the bladder. Such a device may be loaded with solid drug tablets that are "mini-tablets" of reduced size. In a preferred embodiment, the drug tablets are substantially smaller than conventional drug tablets, and unlike conventional tablets that tend to be squat in shape, the drug tablets may be tall and elongated and/or may have flat, rather than convex, end faces. The drug tablets also may constitute mostly drug and little or no excipients, so that the drug tablets contain a large amount of drug considering the tablet size. The drug delivery device may control release of the drug into the body, and therefore the drug tablet may include little or no excipients that control drug release. Instead, the excipients present in the drug tablets may be present primarily or completely to facilitate the tableting process. Thus, the device may provide a very high drug payload on a volume or weight basis, such as at least 50 wt % drug, in contrast to known intravesical devices, such as sponges or reticulated foam structures that may be loaded with as little as 1 to 10 wt % drug.

In particular embodiments, the drug delivery device may deliver lidocaine or another cocaine analogue locally to the bladder over a relatively extended time period for the treatment of a condition such as IC/PBS, neurogenic bladder, or pain such as post-operative pain. In such embodiments, the device may be loaded with lidocaine in solid form, such as in the form of a number of discrete drug tablets. Compositions of such solid drug tablets are provided, along with methods of making the same.

The device may be implanted non-surgically and may deliver drug long after the implantation procedure has ended, both passively and locally. When implanted in the bladder, the device overcomes many deficiencies of conventional treatments, such as delivery via instillation, which must be repeated; delivery via conventional devices, which must be re-filled once implanted; delivery via catheters, which provide a path for bacteria to migrate into the bladder, and systemic delivery, with its associated risk of side effects and reduced drug delivery to the target site. On the contrary, the present device can be implanted once and can release drug over an extended period without surgery or frequent interventions, reducing the opportunity for infection and side effects, increasing the amount of drug delivered locally or regionally to the bladder, and improving the quality of life of the patient during the treatment process.

I. The Implantable Drug Delivery Device

The drug delivery device generally includes two primary parts or portions: the drug reservoir portion and the retention frame portion. The drug reservoir portion may hold the drug to be delivered into the body, and the retention frame portion may facilitate retaining the device in the body.

One example embodiment of a drug delivery device 100 is illustrated in FIG. 1. The device 100 includes a drug reservoir portion 102 and a retention frame portion 104. The drug reservoir portion 102 is attached to discrete points on the retention frame portion 104 but is otherwise separate or spaced apart from the retention frame portion 104. In FIG. 1, the device 100 is shown in a relatively expanded shape suited for retention in the body, and in FIG. 2 the device 100 is shown in a relatively lower-profile shape for deployment through the channel 200 of a deployment instrument, such as a cystoscope or other catheter. Following deployment into the body, the device 100 may assume the relatively expanded shape to retain the drug delivery device in the body cavity or lumen.

For the purposes of this disclosure, the term "relatively higher-profile shape" or "retention shape" generally denotes any shape suited for retaining the device in the intended implantation location, including but not limited to the pretzel shape shown in FIG. 1 that is suited for retaining the device in the bladder. Similarly, the term "relatively lower-profile shape" or "deployment shape" generally denotes any shape suited for deploying the drug delivery device into the body, including the linear or elongated shape shown in FIG. 2 that is suited for deploying the device through the working channel of catheter, cystoscope, or other deployment instrument positioned in a lumen of the body, such as the urethra. In one embodiment, the drug delivery device naturally assumes the relatively expanded shape, in which case the device may be deformed, either manually or with the aid of an external apparatus, into the relatively lower-profile shape for insertion into the body, and once deployed the device may spontaneously or naturally return to the initial, relatively expanded shape for retention in the body.

In particular, the retention frame portion may include a retention frame that retains the device in the body, such as in the bladder. The retention frame may have a certain elastic limit and modulus that allows the device to be introduced into the body in a relatively lower-profile shape but then permits the device to return the relatively expanded shape once inside the body. The device may also have a sufficient elastic modulus to impede the device from assuming the relatively lower-profile shape once implanted, so as to limit or prevent accidentally expulsion of the device from the body under expected forces. For example, the characteristics of the retention frame may be selected to facilitate retaining the device in the relatively expanded shape despite expected forces in the bladder, such as the hydrodynamic forces associated with urination or contraction of the detrusor muscle. Thus, expulsion from the bladder is impeded or prevented so that the device can deliver a drug into the bladder over an extended time period. Such a configuration facilitates delivering a drug such as lidocaine to the bladder over an extending period for the treatment of conditions such as interstitial cystitis, neurogenic bladder, or pain, among others.

Figure 3:
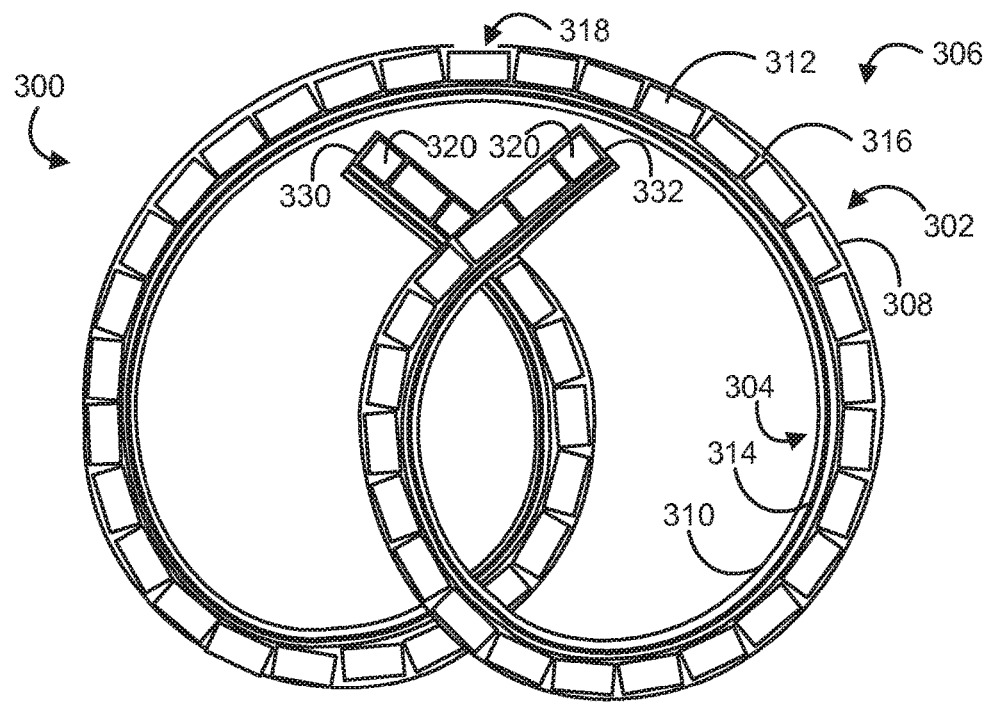
FIG. 3 is a plan view of another embodiment of a drug delivery device.
Figure 4:
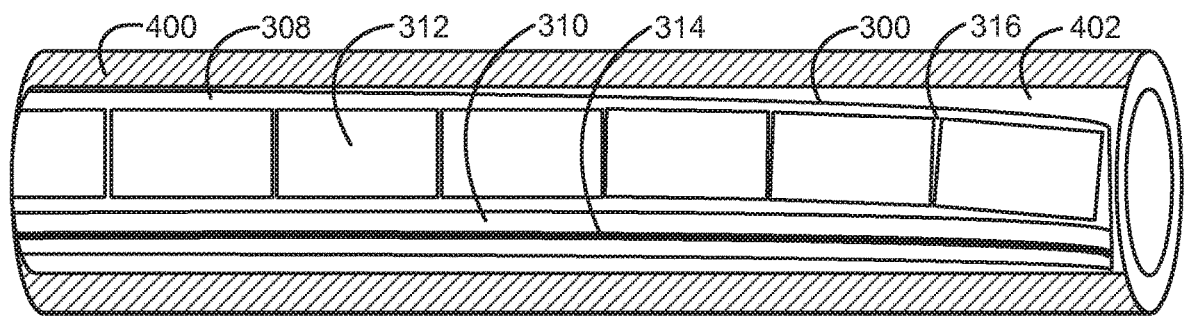
FIG. 4 is a plan view of the drug delivery device shown in FIG. 3, illustrating the drug delivery device inside a deployment instrument.

FIG. 3 illustrates another example embodiment of a drug delivery device 300 that has a drug reservoir portion 302 and a retention frame portion 304, and FIG. 4 illustrates the device 300 in a working channel 402 of a deployment instrument 400. The drug reservoir and retention frame portions 302, 304 of the drug delivery device 300 are longitudinally aligned and are coupled to each other along their length.

In particular, the drug delivery device 300 includes an elastic or flexible device body 306 that defines a drug reservoir lumen 308 and a retention frame lumen 310. The drug reservoir lumen 308 is designed to house a drug formulation, such as a number of solid drug tablets 312, to form the drug reservoir portion 302. The retention frame lumen 310 is designed to house a retention frame 314 to form the retention frame portion 304. The illustrated lumens 308, 310 are discrete from each other, although other configurations are possible.

As shown in the cross-sectional views of FIGS. 5A-5B, the device body 306 includes a tube or wall 322 that defines the drug reservoir lumen 308 and a tube or wall 324 that defines the retention frame lumen 310. The tubes 322, 324 and lumens 308, 310 can be substantially cylindrical, with the drug reservoir lumen 308 having a relatively larger diameter than the retention frame lumen 310, although other configurations can be selected based on, for example, the amount of drug to be delivered, the diameter of the retention frame, and deployment considerations such as the inner diameter of the deployment instrument. The device body 306 may be formed integrally, such as via molding or extrusion, although separate construction and assembly of the tubes 322, 324 is possible. The wall 324 that defines the retention frame lumen 310 may extend along the entire length of the wall 322 that defines drug reservoir lumen 308, so that the retention frame lumen 310 has the same length as the drug reservoir lumen 308 as shown, although one wall may be shorter than the other wall in other embodiments. Further, the two walls 322, 324 are attached along the entire length of the device in the illustrated embodiment, although intermittent attachment can be employed.

As shown in FIG. 3, the drug reservoir lumen 308 is loaded with a number of drug units 312 in a serial arrangement. For example, between about 10 and about 100 drug units 312 may be loaded, such as between about 30 and about 70 drug units 312, or more particularly between about 50 and 60 drug units 312. However, any number of drug units may be used. The drug reservoir lumen 308 includes an entry 330 and an exit 332, which are shown as relatively circular openings at opposite ends of the drug reservoir lumen 308. The entry 330 provides ingress for the drug units 312 to be placed into the drug reservoir lumen 308 during device loading and assembly, such as by a flow of pressurized gas, in which case the exit 332 provides egress for the flow of pressurized gas to escape from the drug reservoir lumen 308. Once the drug units 312 are loaded, at least two end plugs 320 block the entry 330 and exit 332. The end plugs 320 may be cylindrical plugs inserted into the entry 330 and the exit 332, each having a slightly larger outer diameter than an inner diameter of the drug reservoir lumen 308 so that the plugs substantially enclose the entry 330 and exit 332 and are snugly retained in position. In some cases, a number of end plugs 320 can be positioned in the entry 330 or the exit 332. The end plugs 320 also may be omitted, in which case the entry 330 and exit 332 may be closed with a material, such as adhesive, that is placed in the drug reservoir lumen 308 in workable form and cures therein.

In some embodiments, the drug tablets 312 may not fill the entire drug reservoir lumen 308. In such embodiments, a filling material may be used to fill the remainder of the drug reservoir lumen 308. For example, the drug tablets 312 may be loaded in a central portion of the drug reservoir lumen 308 and the filling material may be loaded in the remaining end portions of the drug reservoir lumen 308. The filling material may be inserted into the end portions of the drug reservoir lumen 308 after the lumen is filled with the drug tablets 312. The filling material may be a polymeric adhesive material, such as silicone adhesive. The adhesive may be placed in the drug reservoir lumen 308 in workable form and may cure therein. Suitable adhesives may cure at room temperature or in response to an external stimulus, such as heat. An example of a suitable silicone adhesive is MED3-4213 by Nusil Technology LLC. In some cases, the filling material may enclose the entry 330 and exit 332, in which case the end plugs 320 may or may not be provided. The filling material also may be a number of end plugs 320 inserted into the end portions of the drug reservoir lumen 308.

Once the drug units 312 are loaded, interstices 316 or breaks may be formed between adjacent drug units 312. The interstices or breaks 316 may serve as reliefs that accommodate deformation or movement of the device 300, while permitting the individual drug units 312 to retain their solid form during storage and deployment. Thus, the drug delivery device 300 may be relatively flexible or deformable despite being loaded with a solid drug, as each drug unit 312 may be permitted to move with reference to adjacent drug units 312. Along the length of the device drug reservoir lumen 308, the drug units 312 may have the same composition or may vary in composition, and in some cases drug units 312 of different compositions may be in distinct reservoirs that are segregated, either axially or radially, along the length of the drug reservoir lumen 308.

The retention frame lumen 310 is loaded with the retention frame 314, which may be an elastic wire formed from nitinol or another superelastic or shape-memory material. The retention frame 310 may be configured to spontaneously return to a retention shape, such as the illustrated "pretzel" shape or another coiled shape.

The material used to form the device body 306 may be elastic or flexible to permit moving the device 300 between deployment and retention shapes. When the device is in the retention shape, the retention frame portion 304 may tend to lie inside the drug reservoir portion 302 as shown, although the retention frame portion 304 can be positioned inside, outside, above, or below the drug reservoir portion 302 in other cases. The flexible material also allows the device body 306 to flex outward or circumferentially expand in response to a flow of pressurized gas through the drug reservoir lumen 308 during drug loading, as described below. The material used to form the device body 306 also may be water permeable or porous so that solubilizing fluid can enter the drug reservoir portion 302 to solubilize the drug units 312 once the device is implanted. For example, silicone or another biocompatible elastomeric material may be used.

Although not shown in FIG. 1, the drug delivery device 100 may be loaded with similar drug units, and interstices or breaks may be formed between the drug units so that the device 100 is flexible.

In one embodiment in which the drug delivery device is designed to be implanted in the bladder, the drug delivery device is designed to be inserted into (and optionally retrieved from) the bladder through the urethra cystoscopically. Thus, the device may be sized and shaped to fit through a narrow tubular path of a deployment instrument, such as a catheter or cystoscope. Typically, a cystoscope for an adult human has an outer diameter of about 5 mm and a working channel having a diameter of about 2.4 mm. Thus, the device may be relatively small in size. For example, when the device is elastically deformed to the relatively lower-profile shape, the device for an adult patient may have a total outer diameter that is less than about 2.6 mm, such as less than about 2.4 mm. For pediatric patients, the dimensions of the device may be smaller, such as proportionally smaller based on anatomical size differences and/or on the drug dosage differences between adult and pediatric patients.

In addition to permitting insertion, the relatively small size of the device may also reduce patient discomfort and trauma to the bladder. For example, the relatively small size of the device may reduce irritation of the bladder trigone, which is responsible for creating the sensation of urgency of urination. However, the overall size of the device is larger than the bladder trigone area so that the device cannot become confined or trapped within the trigone area. For example, a bladder of an adult human typically has a capacity of about 500 mL and may have a diameter of about 12.6 cm when full. The trigone region can be approximated as a triangle having a top vertex that represents the bladder neck and two bottom vertices that represent the ureteral orifices. FIG. 7 shows an example triangle T that approximates the trigone of an adult male. In a male, the distance from the bladder neck to one of the ureteral orifices is about 2.75 cm and the distance between the two ureteral orifices is about 3.27 cm. Thus, in FIG. 7, the distance from the top vertex to either of the bottom vertices is about 2.8 cm, while the distance between two bottom vertexes is 3.3 cm. The device 700 may be sized so that when the device 700 overlays the triangle T, substantially the entire triangle T fits within an interior of the device 700. Such sizing ensures the device cannot become trapped in the trigone region. Of course, the size of the device can be varied depending on the size of the animal and the corresponding trigone region. In an adult female, for example, the distance between the two ureteral orifices is about 2.68 cm and the distance from a neck of the bladder to one of the ureteral orifices is about 2.27 cm. Smaller animals may have smaller trigone regions. The device also may have other sizes with respect to the trigone region, however.

The device also may have a density that is less than the density of urine or water, so that the device may float inside the bladder. Such floatation, although not required, may prevent the device from touching the sensitive trigone region of the bladder near the bladder neck. For example, the device may be formed from relatively low density materials of construction, or air or other gas may be entrapped in the device. The outer surface of the device, furthermore, may be soft and smooth without sharp edges or tips.

The exact configuration and shape of the implantable drug delivery device may be selected depending upon a variety of factors including the specific site of deployment or implantation, the route of implantation, the drug and dosage regimen, and the therapeutic application of the device. The design of the device may minimize the patient's pain and discomfort, while locally delivering a therapeutically effective dose of the drug to a tissue site in a patient, such as the urothelial tissue.

The implantable drug delivery device can be made to be completely or partially resorbable so that no explantation, or retrieval, of the device is required following release of the drug formulation. As used herein, the term "resorbable" means that the device, or part thereof, degrades in vivo by dissolution, enzymatic hydrolysis, erosion, or a combination thereof. In one embodiment, this degradation occurs at a time that does not interfere with the intended kinetics of release of the drug from the device. For example, substantial resorption of the device may not occur until after the drug formulation is substantially or completely released. In another embodiment, the device is resorbable and the release of the drug formulation is controlled at least in part by the degradation or erosion characteristics of the resorbable device body. Alternatively, the implantable drug delivery device may be at least partially non-resorbable. In some embodiments, the device is formed from materials suited for urological applications, such as medical grade silicone, natural latex, PTFE, ePTFE, PLGA, PGS, stainless steel, nitinol, elgiloy (non ferro magnetic metal alloy), polypropylene, polyethylene, polycarbonate, polyester, nylon, or combinations thereof.

Following release of the drug formulation, the device and/or the retention frame may be removed substantially intact or in multiple pieces. In one particular embodiment, the device is partially resorbable so that the device, upon partial resorption, breaks into non-resorbable pieces small enough to be excreted from the bladder. Useful biocompatible resorbable and non-resorbable materials of construction are known in the art.

In a preferred embodiment, the drug delivery device is sterilized, such as after the device is manufactured/assembled and before the device is implanted. In some cases, the device may be sterilized after the device is packaged, such as by subjecting the package to gamma irradiation or ethylene oxide gas.

The Drug Reservoir Portion

In one embodiment, the drug reservoir portion of the device includes an elongated tube. An interior of the tube may define one or more drug reservoirs, and a drug formulation may be housed in the drug reservoir(s). In another embodiment, the drug reservoir portion is in a form other than a tube.

The release rate of the drug from the drug reservoir portion generally is controlled by the design of the combination of the device components, including but not limited to the materials, dimensions, surface area, and apertures of the drug reservoir portion, as well as the particular drug formulation and total mass of drug load, among others.

An example of such a drug reservoir portion is shown in FIGS. 8A and 8B. As shown, the drug reservoir portion 800 generally includes a body formed from an elastomeric tube 802. The tube 802 defines a reservoir 804 that contains a number of drug tablets 806. Ends of the tube 802 may be sealed with sealing structures 808, described below. At least one aperture 810 may be disposed in the tube 802. In cases in which an aperture 810 is provided, the aperture 810 may be closed by a degradable timing membrane 812, which may control the initiation of release of the drug formulation from the reservoir. In some cases, a sheath or coating 814 may be positioned about at least a portion of the tube 802 to control or reduce the release rate, such as by reducing the osmotic surface area of the tube or by reducing diffusion through the tube wall. For simplicity, the sheaths or coatings 814 are not shown in FIG. 8B. Additional examples are shown in FIGS. 1-4.

In one embodiment, the drug reservoir portion operates as an osmotic pump. In such embodiments, the tube may be formed from a water permeable material, such as a silicone, or tube may have a porous structure, or both. Following implantation, water or urine permeates through the wall of the tube, enters the reservoir, and is imbibed by the drug formulation. Solubilized drug is dispensed at a controlled rate out of the reservoir through the one or more apertures, driven by osmotic pressure in the reservoir. The delivery rate and overall performance of the osmotic pump is affected by device parameters, such as the surface area of the tube; the permeability to liquid of the material used to form the tube; the shape, size, number and placement of the apertures; and the drug formulation dissolution profile, among other factors. The delivery rate can be predicted from the physicochemical parameters defining the particular drug delivery system, according to well known principles, which are described for example in Theeuwes, *J. Pharm. Sci.,* 64(12): 1987-91 (1975). In some embodiments, the device may initially exhibit a zero-order release rate and subsequently may exhibit a reduced, non-zero-order release rate, in which case the overall drug release profile may be determined by the initial zero-order release rate and the total payload. Representative examples of osmotic pump designs, and equations for selecting such designs, are described in U.S. Patent Publication No. 2009/0149833.

In an alternative embodiment, the device may operate essentially by diffusion of the drug from the tube through (i) one or more discrete apertures formed in the wall of the tube or (ii) through the wall of the tube itself, which may be permeable to the drug or may have a number of pores machined or otherwise formed therethrough for permitting passage of the drug, or (iii) a combination thereof. In embodiments in which diffusion occurs through the wall, the aperture(s) may not be included. An example is provided below in Example 1. In still other embodiments, the device may operate by a combination of osmosis and diffusion.

The drug reservoir portion may be formed from an elastomeric material, which may permit elastically deforming the device for its insertion into a patient, e.g., during its deployment through deployment instrument such as a cystoscope or catheter. For example, the tube may be elastically deformed along with the retention frame for intravesical implantation, as described in further detail below.

In preferred embodiments, the drug reservoir portion is formed from a material that is both elastomeric and water permeable. An example material is silicone that is both elastomeric and water permeable, although other biocompatible materials may be used.

The length, diameter, and thickness of the tube may be selected based on the volume of drug formulation to be contained, the desired rate of delivery of the drug from the tube, the intended site of implantation of the device within the body, the desired mechanical integrity for the device, the desired release rate or permeability to water and urine, the desired induction time before onset of initial release, and the desired method or route of insertion into the body, among others. The tube wall thickness may be determined based on the mechanical properties and water permeability of the tube material, as a tube wall that is too thin may not have sufficient mechanical integrity while a tube wall that is too thick may experience an undesirably long induction time for initial drug release from the device.

In one embodiment, the device body is non-resorbable. It may be formed of a medical grade silicone tubing, as known in the art. Other examples of suitable non-resorbable materials include synthetic polymers selected from poly(ethers), poly(acrylates), poly(methacrylates), poly(vinyl pyrolidones), poly(vinyl acetates), poly(urethanes), celluloses, cellulose acetates, poly(siloxanes), poly(ethylene), poly(tetrafluoroethylene) and other fluorinated polymers, poly(siloxanes), copolymers thereof, and combinations thereof.

In another embodiment, the device body is resorbable. In one embodiment of a resorbable device, the tube of the body is formed of a biodegradable or bioerodible polymer. Examples of suitable resorbable materials include synthetic polymers selected from poly(amides), poly(esters), poly (ester amides), poly(anhydrides), poly(orthoesters), polyphosphazenes, pseudo poly(amino acids), poly(glycerol-sebacate)(PGS), copolymers thereof, and mixtures thereof. In a preferred embodiment, the resorbable synthetic polymers are selected from poly(lactic acids), poly(glycolic acids), poly(lactic-co-glycolic acids), poly(caprolactones), and mixtures thereof. Other curable bioresorbable elastomers include poly(caprolactone) (PC) derivatives, amino alcohol-based poly(ester amides) (PEA) and poly (octane-diol citrate) (POC). PC-based polymers may require additional cross-linking agents such as lysine diisocyanate or 2,2-bis (ε-caprolacton-4-yl)propane to obtain elastomeric properties.

In one embodiment, the material forming the device body may include an "antimicrobial" material, such as a polymer material impregnated with silver or another antimicrobial agent known in the art.

The tube of a drug reservoir portion tube may be substantially linear and in some cases may be substantially cylindrical with a circular cross-section, although square, triangle, hexagon, and other polygonal cross-sectional shapes can be used, among others.

The ends of the tube may be sealed to limit escape of the drug, such as with a sealing structure or other sealing means. The sealing structure may have any shape suited to plug or close the tube end, such as a cylinder 808 as shown in FIG. 8A, a ball, a disk, or others. Additional sealing structures are shown in FIGS. 1 and 3, with FIG. 1 illustrating ball-shaped sealing structures 116 and FIG. 3 illustrating cylindrically shaped sealing structures 320. In some embodiments, the sealing structure may have a larger diameter than the inner diameter of the tube, such that the tube stretches to fit snugly about the sealing structure, closing the tube and retaining the sealing structure in place. An example is shown in FIG. 8A. The sealing structure may be formed from biocompatible material, including a metal such as stainless steel, a polymer such as silicone, a ceramic, sapphire, or adhesive, among others or combinations thereof. The material may be biodegradable or bioerodible. A medical grade silicone adhesive or other adhesive also may be loaded into the tube in a workable form and may then cure within the tube to seal the end.

In some embodiments, the tube may have multiple reservoirs. Each reservoir may be defined by a portion of the tube inner surface and at least one partition. The partition may be a partition structure or plug inserted into the tube, such as a cylinder, sphere, or disk, among others, in which case the partition structure may have a larger cross-section than the tube, securing the partition structure in place and segregating adjacent reservoirs. For example, the cylindrical plug 808 of FIG. 8A that closes the tube end may instead serve as a partition structure to segregate two reservoirs positioned adjacent to each other along the length of the tube. The partition may be non-porous or semi-porous, non-resorbable or resorbable and may be formed of a material described above with reference to the cylindrical plug 808. The partition also may be formed in the tube, such as by molding. For example, one or more webs may extend through the tube along its length to segregate axial reservoirs that extend along the length of the tube, as shown in Examples J through L of FIG. 10. The partition also may be a structure that joins two different tubes that serve as separate reservoirs, as shown in Examples M through O of FIG. 10.

The multiple reservoirs permit segregating two or more different drug formulations in different reservoirs, delivering a single drug from different reservoirs at different rates or times following implantation, or combinations thereof. For example, two different reservoirs may have different configurations, such as different materials, different permeabilities, different numbers or placements of apertures (or the absence of apertures), different timing membranes in the apertures, among others or combinations thereof. The two different reservoirs also may house the same or different drug formulations in the same or different forms (such as liquid, semi-solid, and solid), or combinations thereof. The two different reservoirs further may be configured to release drug via different release mechanisms, such as via osmosis through an aperture and by diffusion through a drug reservoir wall that may lack an aperture completely. Coatings or sheaths also may be provided along different portions of a single drug reservoir or along different drug reservoirs housing the same or different drug formulations. These embodiments can be combined and varied to achieve the desired release profile of the desired drug.

For example, the onset of release of two doses in different reservoirs can be staged by configuring the device accordingly, such as by using different materials for portions of the tube defining different reservoirs, by associating the aperture(s) of different reservoirs with different timing membranes, by placing drugs with different solubilities in the reservoirs, or by placing drugs with different forms in the reservoirs, such as a liquid form for immediate release and a solid form to be solubilized prior to release. Thus, the device may release some drug relatively quickly after implantation while other drug may experience an induction time before beginning release.

In one embodiment, the total volume of the reservoir (or combined reservoirs) is sufficient to contain all the drug needed for local delivery over the course of a single treatment, reducing the number of procedures needed to treat a particular condition.

Apertures

In some embodiments, the device includes one or more apertures or orifices for dispensing the drug, such as via osmosis, diffusion, or a combination thereof, among other. The apertures may be spaced along the tube to provide a passageway for release of the drug formulation. The apertures or orifices may be positioned through a sidewall or an end of the tube. The apertures may be in fluid communication with one or more reservoirs. Embodiments of apertures are shown on the drug reservoir portions in FIGS. 1, 3, and 8A-8B as apertures 114, 318, and 810, respectively.

The aperture may be located about a middle of the drug reservoir portion or adjacent to its exit, which may affect the ease of loading solid drug units into the drug reservoir portion as described below. The apertures may be positioned away from a portion of the tube that will be folded during insertion to limit tearing of degradable membranes on the apertures.

In embodiments in which the device includes a device body that defines both drug reservoir and retention frame lumens, such as the embodiment shown in FIG. 3, the aperture or apertures may have various positions on the wall of the drug reservoir lumen with reference to the wall of the retention frame lumen. For example, as shown in FIG. 5A, the aperture 318 may be formed through the wall 322 of the drug reservoir lumen 308 on an opposite side from the wall 324 of the retention frame lumen 310. Alternatively, as shown in FIG. 5B, the orifice 318 may be formed in a groove or indent defined between the walls 322, 324 of the drug reservoir lumen 308 and the retention frame lumen 310. When the orifice 318 is so positioned, the walls 322, 324 serve as bumpers that impede the orifice 318 from becoming positioned directly adjacent to the implantation site, such as the bladder wall, reducing the likelihood of delivering a large quantity of drug to one particular location. However, such placement may not be necessary, and further, the aperture placement shown in FIG. 5A may be relatively easier to achieve from a manufacturing perspective.

The size, number, and placement of the apertures may be selected to provide a controlled rate of release of the drug. A device that operates primarily as an osmotic pump may have one or more apertures sized small enough to reduce diffusion of the drug through the aperture(s), yet large enough and spaced appropriately along the tube to reduce the buildup of hydrostatic pressure in the tube. Within these constraints, the size and number of apertures for a single device (or reservoir) can be varied to achieve a selected release rate. In exemplary embodiments, the diameter of the aperture is between about 20 μm and about 500 μm, such as between about 25 μm and about 300 μm, and more particularly between about 30 μm and about 200 μm. In one particular example, the aperture has a diameter between about 100 μm and about 200 μm, such as about 150 μm. In embodiments where the device operates primarily by diffusion, the apertures may be in this range or larger. A single device may have apertures of two or more different sizes. The aperture may be circular, although other shapes are possible and envisioned, with the shape typically depending on manufacturing considerations. Examples of processes for forming the apertures include mechanical punching, laser drilling, laser ablation, and molding. The aperture may slightly taper from an exterior to an interior of the tube, and the aperture may be created either before or after the drug is loaded into the tube. The aperture also may be formed in an orifice structure disposed in an end of the tube, such as a ruby or sapphire precision orifice structure from, for example, Bird Precision Orifices, Swiss Jewel Company.

In some embodiments, the drug reservoir portion may not have any apertures, in which case the drug may be released via a release mechanism other than osmosis, such as diffusion through the wall of the drug reservoir portion. Similarly, a drug reservoir portion having multiple discrete drug reservoirs may have apertures associated with all, some, or none of the drug reservoirs, in which cases release from the different drug reservoirs may occur via different release mechanisms.

Degradable Membranes

In one embodiment, a degradable membrane, i.e., a timing membrane, is disposed over or in the apertures (e.g., in register with the aperture) to control the onset of release of the drug formulation. The degradable membrane may be a coating over all or some of the outer surface of the tube or a discrete membrane above or within the aperture. Two or more degradable membranes also may be used to control release from one aperture. The membranes may be formed, for example, of a resorbable synthetic polymer (such as polyester, a poly(anhydride), or a polycaprolactone) or a resorbable biological material (such as cholesterol, other lipids and fats). An example degradable membrane 812 is shown in FIG. 8B, and additional details are described in U.S. Publication No. 2009/0149833.

The Drug Formulation

The drug formulation can include essentially any therapeutic, prophylactic, or diagnostic agent, such as one that would be useful to deliver locally to a body cavity or lumen or regionally about the body cavity or lumen. The drug formulation may consist only of the drug, or one or more pharmaceutically acceptable excipients may be included. The drug may be a biologic. As used herein, the term "drug" with reference to any specific drug described herein includes its alternative forms, such as salt forms, free acid forms, free base forms, and hydrates. Pharmaceutically acceptable excipients are known in the art and may include lubricants, viscosity modifiers, surface active agents, osmotic agents, diluents, and other non-active ingredients of the formulation intended to facilitate handling, stability, dispersibility, wettability, and/or release kinetics of the drug.

In a preferred embodiment, the drug formulation is in a solid or semi-solid form in order to reduce the overall volume of the drug formulation and thereby reduce the size of the device, facilitating implantation. The semi-solid form may be, for example, an emulsion or suspension; a gel or a paste. In many embodiments, the drug formulation desirably includes no or a minimum quantity of excipient for the same reasons of volume/size minimization.

In one embodiment, the drug is a high solubility drug. As used herein, the term "high solubility" refers to a drug having a solubility above about 10 mg/mL water at 37° C. In particular embodiments, the release of the high solubility drug from the drug reservoir is predominately driven by osmotic pressure and occurs via one or more apertures in the sidewall of the elastic tube of the drug reservoir, although other configurations are possible.

In another embodiment, the drug is a low solubility drug. As used herein, the term "low solubility" refers to a drug having a solubility from about 0.1 mg/mL to about 10 mg/mL water at 37° C. In a particular embodiment, the release of the low solubility drug from the drug reservoir is predominately or exclusively diffusion driven and occurs via interconnected passing pores or machined apertures in the sidewall of the elastic tube of the drug reservoir. An example is provided below in Example 1, which describes the release of lidocaine hydrochloride monohydrate, lidocaine base, or both, from devices with one aperture, a number of apertures, or no apertures. In other embodiments, the drug may have a higher or lower solubility. In one embodiment, the drug is formulated to improve its apparent solubility in the implantation environment, such as its apparent solubility in urine within the bladder.

In one embodiment, the implantable drug delivery device is used to provide pain relief to the patient. A variety of anesthetic agents, analgesic agents, and combinations thereof may be used. In one embodiment, the device is used to deliver one or more local anesthetic agents. The local anesthetic agent may be a cocaine analogue. In particular embodiments of the device, the local anesthetic agent is an aminoamide, an aminoester, or a mixture thereof. Combinations of different aminoamides or combinations of different aminoesters are envisioned. Representative examples of possible aminoamides include lidocaine, prilocaine, mepivacaine, bupivacaine, articaine and ropivacaine. Representative examples of possible aminoesters include benzocaine, procaine, proparacaine, and tetracaine. These local anesthetics typically are weak bases and may be formulated as a salt, such as a hydrochloride salt, to render them water-soluble, although the anesthetics also can be used in free base or hydrate form.

In certain embodiments, the analgesic agent includes an opioid. Representative examples of opioid agonists include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated.

Representative examples of other suitable pain relieving agents include such agents include salicyl alcohol, phenazopyridine hydrochloride, acetaminophen, acetylsalicylic acid, flufenisal, ibuprofen, indoprofen, indomethacin, naproxen.

In certain embodiments, the drug delivery device is used to treat inflammatory conditions such as interstitial cystitis, radiation cystitis, painful bladder syndrome, prostatitis, urethritis, post-surgical pain, and kidney stones. Non-limiting examples of specific drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. For kidney stones, the drug(s) may be selected to treat pain and/or to promote dissolution of renal stones.

In one particular embodiment, the drug delivery device is used in association with the placement of a ureteral stent, such as to treat pain, urinary urgency or urinary frequency resulting from ureteral stent placement. Non-limiting examples of specific drugs for such treatment include antimuscarinics, α-blockers, narcotics, and phenazopyridine, among others.

The drug delivery device can be used, for example, to treat urinary incontinence, frequency, or urgency, including urge incontinence and neurogenic incontinence, as well as trigonitis. Drugs that may be used include anticholinergic agents, antispasmodic agents, antimuscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), ZD-6169 (Zeneca Co., United Kingdom), and stilonium iodide.

In another embodiment, the drug delivery device is used to treat urinary tract cancer, such as bladder cancer and prostate cancer. Drugs that may be used include antiproliferative agents, cytotoxic agents, chemotherapeutic agents, or a combination thereof. Representative examples of drugs which may be suitable for the treatment of urinary tract cancer include Bacillus Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may be a biologic, and it may comprise a monoclonal antibody, a TNF inhibitor, an antileukin, or the like. The drug also may be an immunomodulator, such as a TLR agonist, including imiquimod or another TLR7 agonist. The drug treatment may be coupled with a conventional radiation or surgical therapy targeted to the cancerous tissue.

In still another embodiment, the present intravesical drug delivery device is used to treat infections involving the bladder, the prostate, and the urethra. Antibiotics, antibacterial, antifungal, antiprotozoal, antiseptic, antiviral and other antiinfective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In other embodiments, the present drug delivery device is used to treat fibrosis of a genitourinary site, such as the bladder or uterus. Representative examples of drugs for the treatment of fibroids include pentoxphylline (xanthine analogue), antiTNF, antiTGF agents, GnRH analogues, exogenous progestins, antiprogestins, selective estrogen receptor modulators, danazol and NSAIDs.

In various embodiments of treatment methods, the implantable delivery device includes one or more drugs, such as analgesics or anaesthetics, such as lidocaine, bupivacaine, mepivacaine, prilocaine, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; alpha-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., *Spinal Cord* 42:267-72 (2004).

The possible drug useful for treatment of neurogenic bladder may be categorized into one of two general types: those for treating spastic neurogenic bladder and those for treating flaccid neurogenic bladder. In one embodiment, the drug is selected from those known for the treatment of incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include alpha adrenergic agonists, estrogens, beta-adrenergic agonists, tricyclic antidepressants (imipramine, amitriptyline). In still another embodiment, the drug is selected from those known for facilitating bladder emptying (e.g., alpha adrenergic antagonists (phentolamine) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinc agonist, choline ester).

The excipient of the drug formulation may be a matrix material, selected to modulate or control the rate of release of the drug from the reservoir. In one embodiment, the matrix material may be a resorbable or non-resorbable polymer. In another embodiment, the excipient comprises a hydrophobic or amphiphilic compound, such as a lipid (e.g., a fatty acids and derivatives, mono-, di- and triglycerides, phospholipids, sphingolipids, cholesterol and steroid derivatives, oils, vitamins and terpenes). The drug formulation may provide a temporally modulated release profile or a more continuous or consistent release profile. Other drugs and excipients may be used for other therapies.

In some embodiments, the drug formulation is in solid form. For example, the drug formulation may be a number of solid drug units loaded into the drug reservoir portion as described below. The drug formulation also may be loaded into the drug reservoir in workable form and may cure therein. Thereafter, the solidified drug may be broken along the length of the drug reservoir to form the interstices or breaks that permit device deformation. For example, in embodiments in which the drug formulation is configured to be melted and solidified, the drug formulation can be melted, injected into the drug reservoir in melted form, solidified in the drug reservoir, and broken into pieces in the drug reservoir to accommodate device deformation or movement. The drug formulation also may be extruded with the drug reservoir, may cure within the drug reservoir, and subsequently may be broken along the length of the reservoir to accommodate device deformation.

In certain embodiments, the drug formulation is formed into solid drug units that are loaded into the drug reservoir portion. Each of the drug units is a solid, discrete object that substantially retains a selectively imparted shape (at the temperature and pressure conditions to which the delivery device normally will be exposed during assembly, storage, and handling before implantation). The drug units may be in the form of tablets, pellets, or beads, although other configurations are possible. For example, FIG. 6 illustrates a solid drug tablet 312 for implantation, and FIGS. 3 and 4 illustrate a number of the solid drug units 312 loaded into the drug reservoir lumen 308 of the drug delivery device 300.

The drug tablets made by a direct compression tableting process, a molding process, or other processes known in the pharmaceutical arts. The tablets optionally may be coated with one or more materials known in the art for protecting the tablets against destructive exposure to oxygen or humidity during tablet handling, device assembly and storage; for facilitating device loading; for aesthetics; or for facilitating, retarding, or otherwise controlling in vivo dissolution and drug release characteristics.

In a preferred embodiment, each drug unit includes a relatively high weight fraction of the drug and a relatively low weight fraction of excipients. For example, each drug unit may include more than 50% drug by weight. The large ratio of drug load to device size permits loading a therapeutically effective amount of drug into a relatively small device for release over an extended period once implanted. In fact, the drug units may be substantially excipient-free.

In embodiments in which one or more pharmaceutically acceptable excipients are included, the excipients may facilitate loading the solid drug units in the device. For example, the excipients may increase the lubricity of the drug units so that the drug units can slide with reference to the interior lumen walls of the drug reservoir portion. The excipients also may facilitate forming the therapeutic agent or agents into a solid drug tablet that can be loaded into the drug reservoir portion. The excipients also may affect the kinetics of drug release from the device, such as by increasing or retarding the solubility or dissolution rate of the drug units. In some embodiments, however, the drug release rate is predominately controlled by characteristics of the drug reservoir, such as the tube thickness and permeability to water or urine, while the excipient content of the drug units is primarily selected to permit reliable production of drug units that are solid and include a relatively high weight fraction of drug.

The individual drug units may have essentially any selected shape and dimension that fits within the device. In one embodiment, the drug units are sized and shaped such that the drug reservoir portion is substantially filled by a select number of drug units. Each drug unit may have a cross-sectional shape that substantially corresponds to a cross-sectional shape of the drug reservoir portion. For example, the drug units 312 are substantially cylindrical in shape as shown in FIG. 6 for positioning in the substantially cylindrical drug reservoir lumen 308 shown in FIGS. 5A and 5B. Once loaded, as shown in FIG. 3, the drug units 312 substantially fill the drug reservoir lumen 308, forming the drug reservoir portion 302.

The drug units may have outer dimensions that are about the same as, are slightly less than, or slightly exceed inner dimensions of the drug reservoir portion. In embodiments in which the outer dimensions of the drug units exceed the inner dimensions of the drug reservoir portion, the drug units may be loaded into the drug reservoir portion under a flow of pressurized gas that causes the drug reservoir portion to expand outward so that the drug units travel through it. When the flow of pressurized gas is removed, the drug reservoir portion may return to hold the drug units in selected axial positions. Using larger diameter drug units may increase the payload and thus the amount of drug that can be delivered from a drug delivery device of a given size. For example, the drug unit 312 shown in FIG. 6 has an outer diameter that slightly exceeds an inner diameter of the drug reservoir lumen 308 shown in FIGS. 5A and 5B. Such drug units 312 may be loaded into the lumen 308 under a flow of pressurized gas that radially expands the drug reservoir wall 322 so that the drug units 312 may travel through the drug reservoir lumen 308 in an axial direction, and when the flow of pressurized gas is removed, the wall 322 may return to retain the drug units 312 in selected axial positions along the length of the lumen 308, as shown in FIG. 3. In embodiments in which the outer dimensions of the drug units are smaller than the inner dimensions of the drug reservoir portion, the drug units may have reduced contact with the drug reservoir portion. Therefore, the drug units may be loaded using a flow of pressurized gas at relatively lower pressure, as the flow of pressurized gas may not need to overcome the force of friction.

In embodiments, the drug units are shaped to align in a row when housed in the drug reservoir. Each drug unit has a cross-sectional shape that corresponds to the cross-sectional shape of the drug reservoir, and each drug unit may have end face shapes that correspond to the end faces of adjacent drug units. Thus, once the drug tablets are loaded in the drug reservoir, the line or row of drug tablets may substantially fill the drug reservoir with interstices or breaks formed between adjacent drug units. The interstices or breaks accommodate deformation or movement of the device, such as during deployment, while permitting the individual drug units to retain their solid form. Thus, the drug delivery device may be relatively flexible or deformable despite being loaded with a solid drug, as each drug unit may be permitted to move with reference to adjacent drug units.

An example is shown in FIG. 6, which illustrates the drug unit 312 having circular flat end faces 326 and a cylindrical side wall 328. Thus, the drug unit 312 can be aligned in a row with other drug units 312 for loading into the cylindrical drug reservoir lumen 308 as shown in FIGS. 3 and 4. When so loaded, the drug units 312 substantially fill the drug reservoir lumen 308, with interstices or breaks 316 formed between them to accommodate deformation or movement. The flat end faces 326 permit piecewise flexibility of the device while limiting the volume or space within the drug reservoir portion that is devoted to the interstices or breaks 316. Thus, the device can be substantially filled with solid drug while retaining its flexibility. Loading the device with a number of drug tablets 312, such as drug tablets that are relatively uniform in size and shape, beneficially permits manufacturing a device that behaves as expected in response to expected forces during and after implantation and exhibits expected drug release characteristics once implanted. That is, the tablet uniformity advantageously enables reproducibility in producing the medical product and thereby generally provides reliable, repeatable drug release characteristics.

In some embodiments, the drug units are relatively tall and slender, unlike conventional drug tablets that tend to be short and squat. The drug units may be tall enough to retain their orientation once loaded in the drug reservoir, with reduce tipping or rolling. On the other hand, the drug units may be short enough to provide enough interstices or breaks so that the device can flex or move along its length. In particular, each drug unit may have a length that exceeds its width, meaning an aspect ratio of height:width that is greater than 1:1. Suitable aspect ratios for the drug units may be in the range of about 3:2 to about 5:2, although other aspect ratios are possible, including aspect ratios that are less than 1:1, like conventional drug tablets. An example is shown in FIG. 6, which illustrates the drug unit 312 with a length that exceeds its diameter.

In embodiments in which the solid drug tablets are designed for insertion or implantation in a lumen or cavity in the body, such as the bladder, via a drug delivery device, such as a device of the type described above with reference to FIG. 3, the drug tablets may be "mini-tablets" that are suitably sized and shaped for insertion through a natural lumen of the body, such as the urethra. For the purpose of this disclosure, the term "mini-tablet" generally indicates a solid drug tablet that is substantially cylindrical in shape, having end faces that are relatively planar or flat and a side face that is substantially cylindrical.

An example mini-tablet is shown in FIG. 6. The mini-tablet 312 has a diameter, extending along the end face 326, in the range of about 1.0 to about 3.2 mm, such as between about 1.5 and about 3.1 mm. The mini-tablet 312 has a length, extending along the side face 328, in the range of about 1.7 mm to about 4.8 mm, such as between about 2.0 mm and about 4.5 mm. The friability of the tablet may be less than about 2%. Embodiments of solid drug tablets and systems and methods of making the same are further described below with reference to FIG. 11.

The Retention Frame Portion

The drug delivery device may include a retention frame portion. The retention frame portion is associated with the drug reservoir portion and permits retaining the drug reservoir portion in the body, such as in the bladder. The retention frame portion may include a retention frame that is deformable between a relatively expanded shape and a relatively lower-profile shape. For example, the retention frame may naturally assume the relatively expanded shape, may be manipulated into the relatively lower-profile shape for insertion into the body, and may spontaneously return to the relatively expanded shape upon insertion into the body. The retention frame in the relatively expanded shape may be shaped for retention in a body cavity, and the retention frame in the relatively lower-profile shape may be shaped for insertion into the body through the working channel of a deployment instrument such as a catheter or cystoscope. To achieve such a result, the retention frame may have an elastic limit, modulus, and/or spring constant selected to impede the device from assuming the relatively lower-profile shape once implanted. Such a configuration may limit or prevent accidental expulsion of the device from the body under expected forces. For example, the device may be retained in the bladder during urination or contraction of the detrusor muscle.

In a preferred embodiment, the retention frame includes or consists of an elastic wire. In one embodiment, the elastic wire may comprise a biocompatible superelastic alloy or other shape-memory material, such as a nickel-titanium alloy (e.g., Nitinol), a titanium-molybdenum alloy (e.g., Flexium), or a biodegradable shape memory polymers described in U.S. Pat. No. 6,160,084 to Langer et al. The elastic wire also may include a relatively low modulus elastomer, which may be relatively less likely to irritate or cause ulcer within the bladder or other implantation site and may be biodegradable so that the device need not be removed. Examples of low modulus elastomers include polyurethane, silicone, styrenic thermoplastic elastomer, and poly(glycerol-sebacate) (PGS). The elastic wire may be coated with a biocompatible polymer, such as a coating formed from one or more of silicone, polyurethane, styrenic thermoplastic elastomer, Silitek, Tecoflex, C-flex, and Percuflex.

Figure 2:
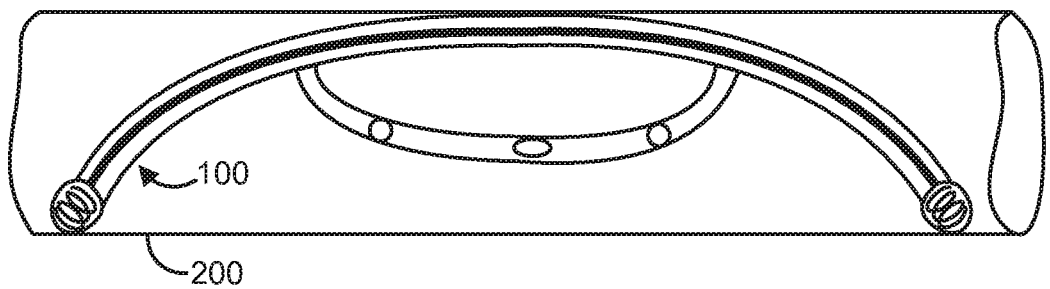
FIG. 2 is a plan view of the drug delivery device shown in FIG. 1, illustrating the drug delivery device inside a deployment instrument.

For example, in the embodiment shown in FIGS. 1-2, the retention frame 104 includes an elastic wire 106 formed from a superelastic alloy, such as nitinol, and covered in a polymer coating 108, such as a silicone sheath. Similarly, in the embodiment shown in FIGS. 3-4, the retention frame 314 is an elastic wire formed from a superelastic alloy, such as nitinol, and surrounded by the wall 324 of the retention frame lumen 310, which forms a protective sheath about the retention frame 314. Thus, the wall 324 may be formed from a polymer material, such as a silicone.

In some embodiments, the retention frame lumen 310 may include the retention frame 314 and a filling material, such as a polymer filling. An example filling material is a silicone adhesive, such as MED3-4213 by Nusil Technology LLC, although other filling materials may be used. The filling material may fill the void in the retention frame lumen 310 about the retention frame 314. For example, the filling material may be poured into the retention frame lumen 310 about the retention frame 314 and may cure therein. The filling material may reduce the tendency of the drug reservoir lumen 308 to stretch along, or twist or rotate about, the retention frame 314, while maintaining the drug reservoir lumen 308 in a selected orientation with reference to the retention frame 314. The filling material is not necessary, however, and may be omitted.

When the retention frame is in the relatively expanded shape, such as the coiled shapes shown in FIGS. 1 and 3, the device may occupy a space having dimensions suited to impede expulsion from the bladder. When the retention frame is in the relatively lower-profile shape, such as the elongated shapes shown in FIGS. 2 and 4, the device may occupy an area suited for insertion into the body, such as through the working channel of a deployment instrument. The properties of the elastic wire cause the device to function as a spring, deforming in response to a compressive load but spontaneously returning to its initial shape once the load is removed. The polymer coating may make the outer surface of the retention frame relatively smooth and soft, reducing irritation of the bladder or other implantation site.

A retention frame that assumes a pretzel shape may be relatively resistant to compressive forces. The pretzel shape essentially comprises two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination.

In embodiments in which the retention frame comprises a shape-memory material, the material used to form the frame may "memorize" and spontaneously assume the relatively expanded shape upon the application of heat to the device, such as when exposed to body temperatures upon entering the bladder.

Figure 9:
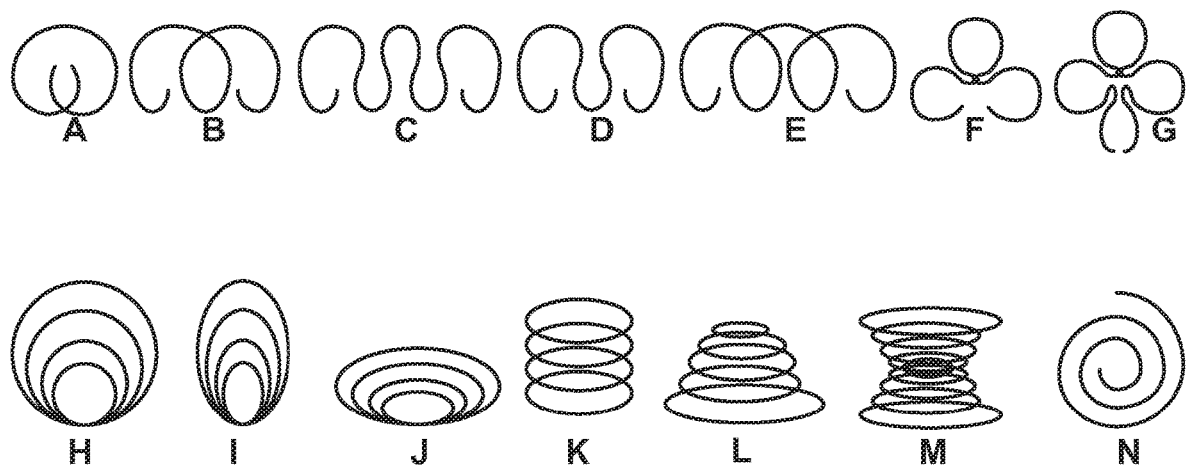
FIG. 9 illustrates example shapes for a retention frame of a drug delivery device.

The retention frame may be in a form having a high enough spring constant to retain the device within a body cavity, such as the bladder. A high modulus material may be used, or a low modulus material such as polyurethane or silicone. Especially when a low-modulus material is used, the retention frame may have a diameter and/or shape that provides a spring constant without which the frame would significantly deform under the forces of urination. For example, the retention frame may include one or more windings, coils, spirals, or combinations thereof, specifically designed to achieve a desirable spring constant, such as a spring constant in the range of about 3 N/m to about 60 N/m, or more particularly, in the range of about 3.6 N/m to about 3.8 N/m. Such a spring constant may be achieved by one or more of the following techniques: increasing the diameter of the elastic wire used to form the frame, increasing the curvature of one or more windings of the elastic wire, and adding additional windings to the elastic wire. The windings, coils, or spirals of the frame may have a number of configurations. For example, the frame may be in a curl configuration comprising one or more loops, curls or sub-circles. As shown in Examples A through G of FIG. 9, the curls may be connected linearly or radially, may turn in the same or alternating directions, and may or may not overlap. The ends of the elastic wire may be adapted to avoid tissue irritation and scarring, such as by being soft, blunt, inwardly directed, joined together, or a combination thereof. The frame may also include one or more circles or ovals arranged in a two-dimensional or a three-dimensional configuration. As shown in Examples H through M of FIG. 9, the frame may include a number of concentric ovals or circles, either closed or opened, the same or different sizes, overlapping or not overlapping, and joined together at one or more connecting points. The frame may be an open-ended spiral, as shown in Example N, or a spiral having closed ends.

Other Device Features

The drug reservoir portion can include a coating or a sheath, which may be substantially impermeable to water or relatively less permeable to water than the drug reservoir portion to reducing or alter the osmotic or diffusive surface area of the device body. Thus, the release rate can be independently controlled or targeted with reduced adjustment of desired device characteristics, such as size, shape, material, permeability, volume, drug payload, flexibility, and spring constant, among others. To achieve the release rate, the coating or sheath may cover all or any portion of the device body, and the coating or sheath may be relatively uniform or may vary in thickness, size, shape, position, location, orientation, and materials, among others and combinations thereof. Further, multiple coatings or sheaths may be provided along different portions of the device body, about the same drug reservoir or different drug reservoirs housing the same or different drug formulations. In cases in which the drug reservoir portion is formed from silicone tubing, an example coating may be formed from parylene, while an example sheath may be formed from a polymer such as polyurethane or curable silicone, or another biocompatible coating or sheath material known in the art. In some embodiments, the coating or sheath may be positioned on the tube between the end and the orifice so that water permeating through the tube adjacent to the end can drive through the portion of the tube covered by the sheath and out of the orifice, reducing or avoiding isolation or stagnation of the drug under the sheath. Example sheaths are 814 illustrated in FIG. 8A. Coatings and sheaths, and equations for selecting such designs, are described in U.S. Patent Publication No. 2009/0149833.

In one embodiment, the device includes at least one radio-opaque portion or structure to facilitate detection or viewing (e.g., by X-ray imaging or fluoroscopy) of the device by a medical practitioner as part of the implantation or retrieval procedure. In one embodiment, the tube is constructed of a material that includes a radio-opaque filler material, such as barium sulfate or another radio-opaque material known in the art. Silicone tubing may be made radio-opaque by blending radio-opaque fillers, such as barium sulfate or another suitable material, during the processing of the tubing. The radio-opaque material also may be associated with the retention frame. For example, as shown in FIGS. 1-2, a platinum wire 110 may be wound about ends of the elastic wire 106 and covered in smoothening material 112. Ultrasound imaging may be used. Fluoroscopy may be the preferred method during deployment/retrieval of the non-resorbable device by providing accurate real-time imaging of the position and orientation of the device to the practitioner performing the procedure.

In one embodiment, the body of the implantable drug delivery device further includes at least one retrieval feature, such as a structure that facilitates removal of the device from the body cavity, for example for removal of a non-resorbable device body following release of the drug formulation.

One example retrieval feature is a string, formed of a biocompatible material. The string may be attached to a mid-portion or an end-portion of the drug delivery device. In some embodiments, the string is sized to extend along the urethra from the bladder to the exterior of the body, in which case a proximal end of the string may be positioned outside of the body once the device is positioned in the bladder. The string also may be shorter in size, so that once the device is positioned in the bladder, the proximal end of the string is positioned in the urethra in a location that is reachable by a physician. In either case, the device may be removed from the bladder by engaging the string to pull the device through the urethra. In such embodiments, the diameter of the string may be sized to fit comfortably in the urethra during the period of implantation. In other embodiments, the string is sized to be wholly implanted in the bladder with the device, in which case the string facilitates locating and grasping the device within the bladder using a removal instrument positioned in the urethra, such as a cystoscope or catheter.

In embodiments in which the string is attached to a mid-portion of the drug delivery device, the device may fold upon itself as it enters the removal instrument or the urethra. Folding at the mid-portion may be facilitated once the drug delivery device has released at least a portion of the drug or is empty. In embodiments in which the string is attached to an end-portion of the drug delivery device, the device may move into the deployment shape as it enters the removal instrument or the urethra. Thus, the deployment shape also may be considered a retrieval shape in such embodiments.

Embodiments of retrieval features are described in U.S. Patent Publication No. 2007/0202151 A1. In these and in other embodiments, the device may be retrieved using conventional endoscopic grasping instruments, such as alligator forceps, three or four-pronged optical graspers. For example, if the device has an O-shaped or coiled portion, the removal of the device can be facilitated by those grasping instruments.

Combination of the Components

The drug reservoir portion and the retention frame portion are associated with each other to form the drug delivery device. A variety of different associations are envisioned. For example, the drug reservoir portion may be attached to an intermediate region of the retention frame. The drug reservoir portion may have first and second end portions that are attached to an intermediate region of the retention frame. The end portions of the drug reservoir may terminate at the vesical retention frame, the end portions may overlap the vesical retention frame, or a combination thereof. FIGS. 1-2 illustrate an example of one such device 100. The drug reservoir portion may be oriented with reference to the retention frame portion such that the drug reservoir portion lies within the perimeter of the retention frame portion, beyond the perimeter of the retention frame portion, or a combination thereof. Additionally, a number of drug reservoir portions may be associated with a single retention frame portion, as shown in Examples A through E of FIG. 10.

Figure 10:
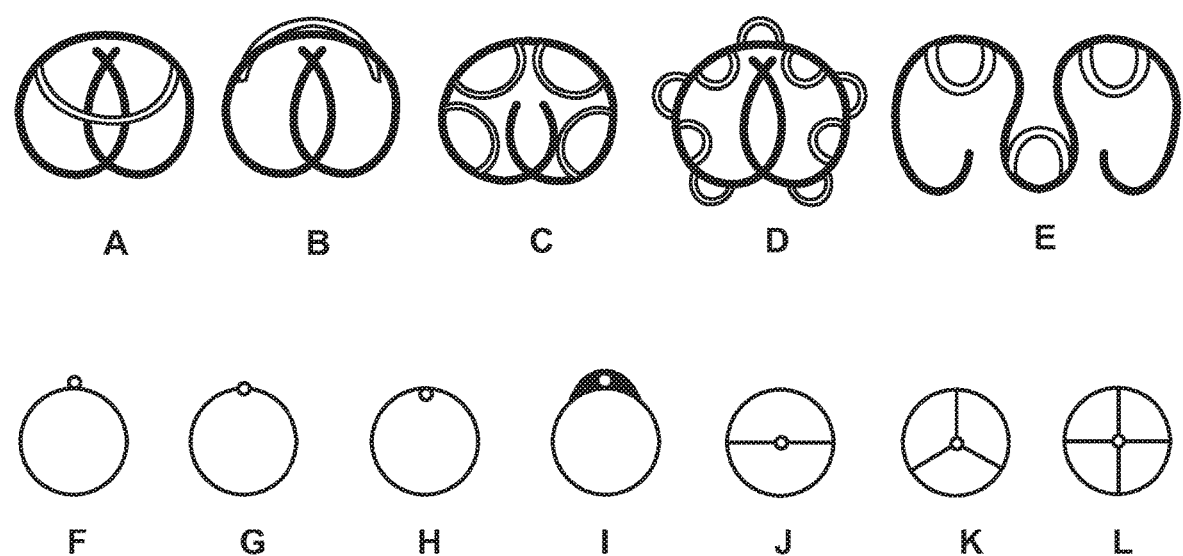
FIG. 10 illustrates example configurations for drug delivery devices having at least one drug delivery portion and a retention frame portion.

In other embodiments, the drug reservoir portion and the retention frame portion are at least partially aligned. In other words, the drug reservoir portion may extend along a portion or the entire length of the retention frame portion, substantially parallel or coincident with the retention frame portion. Examples of such embodiments are shown in FIG. 10, which illustrates several alternative embodiments in cross-section. As shown in Examples F, G, H, and I, the retention frame wire may extend along either an exterior surface of the drug reservoir wall, along an interior surface of the drug reservoir wall, through the drug reservoir wall, or within a reinforced area inside or outside of the wall. As shown in Examples J, K, and L, the elastic wire may also be positioned within the interior of the tube supported by a web, which may partition the tube into multiple compartments. The web may be perforated or otherwise non-continuous so that the compartments are in communication with each other, or the web may be relatively continuous such that the compartments are segregated from each other to form different reservoirs that may be suited for holding different drug formulations. The web may be formed from the same material as the tube, or from a material having a different permeability to water or urine, depending on the embodiment. As shown in Examples M, N, and O, the elastic wire may be associated with multiple tubes, extending along or between the tubes. The elastic wire may be embedded in a reinforcement area that joins together multiple discrete tubes. The tubes may hold the same or different drug formulations and also may be formed from the same or different materials of construction, such as materials that differ in permeability to urine or other aqueous or bodily fluids.

In other embodiments, the drug reservoir portion and the retention frame portion may be the same component in some embodiments. In such cases, the device may comprise a silicone tubing formed in a configuration having a sufficient spring constant to retain the device in the body, as described above. Also, the drug reservoir portion may be wrapped around the retention frame portion, one or any number of times.

The embodiments described herein may be combined and varied to produce other drug delivery devices that fall within the scope of the present disclosure. For example, the drug reservoir portion may be attached to any portion of the retention frame portion in any manner. Multiple drug reservoir portions may be provided, a single drug reservoir portion may be partitioned, or a combination thereof, which may facilitate delivering multiple different drugs into the body, delivering different forms of drugs into the body, delivering drugs at varying rates into the body, or a combination thereof.

In the embodiment shown in FIG. 3, for example, the drug delivery device 300 is suited for delivering a drug into the bladder. The drug reservoir lumen 308 may have an inner diameter of about 1.3 to about 3.3 mm, such as about 1.5 to about 3.1 mm, an outer diameter of about 1.7 to about 3.7 mm, such as about 1.9 to about 3.4 mm, and a length of about 12 to 21 cm, such as about 14 to 16 cm. The drug reservoir lumen 308 may hold about 10 to 100 cylindrical drug tablets, such mini-tablets. The mini-tablets may each having a diameter of about 1.0 to about 3.3 mm, such as about 1.5 to about 3.1 mm, and a length of about 1.5 to about 4.7 mm, such as about 2.0 to about 4.5 mm. Such mini-tablets may have a lidocaine payload of about 3.0 to about 40.0 mg. One particular example mini-tablet may have a diameter of about 1.52 mm, a length of about 2.0 to 2.2 mm, and a mass of about 4.0 to 4.5 mg lidocaine. Another particular example mini-tablet may have a diameter of about 2.16 mm, a length of about 2.9 to 3.2 mm, and a mass of about 11.7 to 13.1 mg lidocaine. Yet another particular example mini-tablet may have a diameter of about 2.64 mm, a length of about 3.5 to 3.9 mm, and a mass of about 21.3 to 23.7 mg lidocaine. Still another particular example mini-tablet may have a diameter of about 3.05 mm, a length of about 4.1 to 4.5 mm, and a mass of about 32.7 to 36.9 mg lidocaine. However, other diameters, lengths, and masses can be used.

Within these ranges, the device may be designed to deliver between about 150 mg and 1000 mg of lidocaine to the bladder, such as about 200 mg, about 400 mg, about 600 mg, or about 800 mg of lidocaine. For example, a smaller payload may be delivered from a smaller device or from a device loaded with fewer tablets, the remainder of the space in the device being loaded with a spacer or filling material. The end plugs 320 may be silicone plugs having an outer diameter sized accordingly.

The foregoing specific configurations are merely possibilities of the type of devices that may be created by a person skilled in the art upon reading the present disclosure.

II. Solid Drug Tablets

In a preferred embodiment, the solid drug tablets have a relatively high drug or API (active pharmaceutical ingredient) content by weight, which may be particularly well suited for use with an implantable drug delivery device. After the drug delivery device is implanted, the drug tablets are solubilized in the device, and the drug is released from the device into the body cavity or lumen, such as the bladder. For example, the drug delivery device may operate as an osmotic pump that continuously releases drug into the vesical over an extended period as the drug tablets are solubilized in the device. As another example, the drug delivery device may operate by diffusion, which causes continuous release of the drug into the vesical over an extended period as the drug tablets are solubilized in the device.

In order to maximize the amount of drug that can be stored in and released from a given drug delivery device of a selected (small) size, the drug tablet preferably comprises a high weight fraction of drug or API, with a reduced or low weight fraction of excipients as are required for tablet manufacturing and device assembly and use considerations. For the purposes of this disclosure, terms such as "weight fraction," "weight percentage," and "percentage by weight" with reference to drug, or API, refers to the drug or API in the form employed, such as in salt form, free acid form, free base form, or hydrate form. For example, a drug tablet that has 90% by weight of a drug in salt form may include less than 90% by weight of that drug in free base form.

In one embodiment, the drug tablet is more than 50% by weight drug. In a preferred embodiment, 75% or more of the weight of the drug tablet is drug, with the remainder of the weight comprising excipients, such as lubricants and binders that facilitate making the drug tablet. For the purposes of this disclosure, the term "high weight fraction" with reference to the drug or API means that excipients constitute less than 25 wt %, preferably less than 20 wt %, more preferably less than 15 wt %, and even more preferably less than 10 wt % of the drug tablet.

In one embodiment, the drug and excipients are selected and the tablet formulated to be water soluble, so that the drug tablets can be solubilized within the vesical to release the drug. In a preferred embodiment, the drug tablets are formulated to be sterilizable, either within or outside of the drug delivery device, without substantial or detrimental changes in the chemical or physical composition of the drug tablets. Such drug tablets may be quite different from conventional drug tablets, which typically include active ingredients that constitute less than 50% of the drug tablet content by weight, with the remainder of the drug tablet comprising excipients that are often insoluble and/or may not be suited for conventional sterilization. Furthermore, the present drug tablets may be sized and shaped for use with an implantable drug delivery device. For example, the drug tablets may be "mini-tablets" that are much smaller in size than conventional tablets, which may permit inserting the drug tablets through a lumen such as the urethra into a cavity such as the bladder. An embodiment of a solid drug tablet 312 for intravesical insertion or other in vivo implantation is shown in FIG. 6.

The drug tablet includes a drug content and may include an excipient content. The drug content includes one or more drugs, while the excipient content includes one or more excipients. By weight, the drug content constitutes a relatively higher percentage of the drug tablet than the excipient content. In some cases, the drug content comprises about 75% or more of the weight of the drug tablet. More particularly, the drug content may comprise about 80% or more of the weight of the drug tablet. For example, the drug content may comprise between about 85% and about 99.9% of the weight of the drug tablet. In some embodiments, the excipient content can be omitted completely. The term "excipient" is known in the art, and representative examples of excipients useful in the present drug tablets may include ingredients such as binders, lubricants, glidants, disintegrants, colors, fillers or diluents, coatings and preservatives, as well as other ingredients to facilitate manufacturing, storing, or administering the drug tablet.

In one embodiment, the drug content includes at least one local anesthetic agent. The local anesthetic agent can be selected from the amide class of anesthetics, the ester class of anesthetics, or some combination thereof. Examples of amide-class anesthetics include articaine, bupivacaine, carticaine, cinchocaine, etidocaine, levobupivacaine, lidocaine, mepivacaine, prilocaine, ropivacaine, and trimecaine. Examples of the ester-class anesthetics include amylocaine, benzocaine, butacaine, chloroprocaine, cocaine, cyclomethycaine, dimethocaine, hexylcaine, larocaine, meprylcaine, metabutoxycaine, orthocaine, piperocaine, procaine, propoxycaine, proxymetacaine, risocaine, and tetracaine. Other anesthetics, such as lontocaine, also may be used. The drug content may include other drugs described herein, alone or in combination with a local anesthetic agent. The local anesthetic agent could be an antimuscarinic compound that exhibits an anesthetic effect, such as oxybutynin or propiverine.

In a preferred embodiment, the drug tablets include lidocaine. A drug delivery device having drug tablets that primarily comprise lidocaine may be wholly deployed in the bladder of a patient in need of treatment for interstitial cystitis, neurogenic bladder, or pain, among others. Other diseases or conditions may also be treated using this device. In other embodiments, other drugs, alone or in combination with lidocaine, may be used to treat interstitial cystitis or other diseases and conditions involving the bladder.

In making the drug tablets, the drug and optional excipients may initially be in the form of compactable powders or blended powders. The drug and optional excipients preferably are selected to be capable of withstanding a sterilization procedure without undesirable changes in chemical composition or physical characteristics. These powdered ingredients can be compressed into solid drug tablets, which increase the mass of drug that can be delivered from a tablet of a given volume/size. In one embodiment, the anesthetic agent or other drug is in the form of a water soluble salt. For example, the lidocaine may be in the form of a hydrochloride monohydrate. In another embodiment, the lidocaine may be in the form of a lidocaine base.

In a preferred embodiment, the drug tablet has an excipient content that includes at least one binder, lubricant, or a combination thereof. A binder holds particles of the composition together, while a lubricant prevents particles of the composition from adhering to components of the manufacturing apparatus, such as dies and punches of a tablet press. The binders and/or lubricants can be combined with the drugs to form the solid drug tablet in a variety of manners. In some cases, the excipients and drugs are blended and compressed using direct compression. In such cases, the excipient content can include a binder, a lubricant, or both. Each excipient may be in dry powder form, and these powders are blended to form a composition that is compressed.

In other cases, the drug powder may be granulated before the drug tablet is made from it. In such cases, the excipient content may include both a binder and a lubricant. The binder may be used to increase the drug particle size before formation of the drug tablet, while the lubricant is used to reduce friction between the tablet and components of the manufacturing apparatus during the tableting process. For example, the drug may be combined with the binder to form granules, the granules can be blended with the lubricant, and the resulting composition may be compressed using a tableting machine. Due to the increased particle size that results from granulating the drug with the binder, the drug tablet can be manufactured using a smaller quantity of lubricant, which may decrease the overall quantity of excipient required to form a solid drug tablet using a stable manufacturing process. In such cases, the excipients may be in dry powder or liquid form, depending on how the excipient is to be incorporated into the mixture. For example, the binder content may be a dry powder that is mixed with the drug, or a solution that is sprayed on drug. Embodiments of methods of making a solid drug tablet are described in further detail below with regard to FIG. 11.

The excipient content is selected so that a suitable manufacturing process can be used to form tablets that are suitable for the intended use. Particularly, the composition of the excipient content, the characteristics of the excipient content, such as the quantity, solubility, and moisture level of the excipient content, and the mode of incorporating the excipient content into the drug content are specifically selected. The selected excipient content permits compressing the drugs into a solid drug tablet with suitable compression and injection forces and without unsuitable buildup on components of the manufacturing equipment, such as the table and dies. The selected excipient content also constitutes a minor fraction of the drug tablet by weight. In one embodiment, the drug tablets formed with the selected excipient content can be sterilized (before or after being loaded into a drug delivery device), have a commercially reasonable shelf life, are appropriate in composition for the intended route of administration, are stable in the intended environment in vivo, and provide the required drug release kinetics in vivo.

In various embodiments, the excipient content may be selected based on manufacturing considerations and/or to produce a drug tablet having a suitable solubility or dissolution characteristics, which in conjunction with the structural and material characteristics of the drug reservoir component (e.g., the material and structure of the elastic tube) determine the drug release profile provided by the implantable device.

In particular embodiments, the excipients include a water soluble binder and a water soluble lubricant. Water soluble excipients facilitate solubilization of the drug tablet in vivo, e.g., following intravesical deployment. In a preferred embodiment, the water soluble excipient is one that will not clog a release orifice of a drug delivery device of the type described hereinabove. Examples of suitable, water soluble binders include polyvinylpyrrolidone (i.e., povidone or PVP), a poly(ethylene glycol) (PEG), a poly(ethylene oxide) (PEO), a poloxamer, hydroxypropyl cellulose (HPC), other binders, or combinations thereof. Examples of suitable, water soluble lubricants include leucine, sodium lauryl sulfate, sucrose stearate, boric acid, sodium acetate, sodium oleate, sodium stearyl fumarate, and PEG. Other binders and lubricants also can be used, either alone or in combination with the water soluble binders and lubricants provided above, especially if such other binders and lubricants satisfy the additional criteria outlined above.

In a particular embodiment, the binder is povidone. Povidone is highly adhesive in relatively low volumes, which facilitates creating a solid drug tablet having a relatively high concentration of drugs. Povidone is particularly suited for agglomerating drugs using, for example, a wet granulation process, which may reduce the amount of lubricant needed to form the drugs into a solid drug tablet. Solid tablets made using povidone are often hard and non-friable. Povidone also is generally soluble, which may be particularly advantageous for drug tablets that are designed to be implanted intravesically in a drug delivery device, such as an osmotic drug delivery device implanted into an aqueous environment, such as found in the bladder. Povidone may facilitate a reliable dissolution rate of a solid drug tablet, and may enhance the solubilization of a dissolution-limited drug from the drug tablet. Povidone also tolerates changes in pH and is stable in acidic conditions, which may make povidone particularly suitable for inclusion in drug tablets designed for implantation in the bladder. Povidone also is resistant to interaction with ionic drug actives and their salts. Povidone is available in a range of different "K-values," which generally correlate to molecular weights. Povidone with a K-value in the range of 29-32 may be suited for use in the present embodiments, although povidone having other K-values can be used. Examples of commercially available povidone products include Plasdone®, (International Specialty Products, Wayne, N.J.) and Kollidon™ (BASF Corporation, Florham Park, N.J.).

In one particular embodiment, the binder is HPC. An example of commercially available HPC is Klucel® (Aqualon, Wilmington, Del.).

In other embodiments, other binders may be used alone or in combination with povidone or HPC. Some binders can be used to create drug tablets that are only suited for use with certain patients or therapeutic indications. For example, sodium laurel sulfate may be suitable for creating solid drug tablets, but such drug tablets may negatively interact with wounds or lesions, if present, in the bladder wall.

In one particular embodiment, the lubricant comprises or consists of PEG having a molecular weight between about 4,000 to 20,000, preferably between about 6,000 to about 8,000. Representative examples include PEG 20M, PEG 3350, PEG 6000, PEG 8000, and MPEG-5000. In a preferred embodiment, the lubricant is PEG 8000, which is generally a waxy, free-flowing powder, which facilitates the drug tableting processes. PEG 8000 has a melting temperature suitable for use in drug tablets that are implanted in a body cavity or lumen for continuous release over an extended period. In other embodiments, other lubricants may be used alone or in combination with a PEG, such as PEG 8000.

In some cases, the drug content includes lidocaine hydrochloride monohydrate or another suitable local anesthetic agent, while the excipient content includes a binder content and a lubricant content. The drug content can be primarily or completely lidocaine hydrochloride monohydrate alone. The binder content can comprise a binder such as povidone, and in some cases the binder content can be primarily or completely povidone alone. The lubricant content can comprise a lubricant such as a high-molecular weight form of PEG, and in some cases the lubricant content can be primarily or completely PEG alone, such as PEG 8000.

In such embodiments, the drug content can constitute at least 75%, and more particularly between about 85% to 95% of the drug tablet by weight, such as between about 88% and about 96% of the drug tablet by weight, and in some cases between about 89% and about 92% of the drug tablet by weight. The binder content can constitute between about 1% to 10% of the drug tablet by weight, such as between about 2% and about 3% of the drug tablet by weight, and in some cases between about 2.3% and about 2.7% of the drug tablet by weight. The lubricant content can constitute between about 1% to 11% of the drug tablet by weight, such as between about 4% and about 9% of the drug tablet by weight, and in some cases between about 5.5% and about 8.5% of the drug tablet by weight. In these embodiments, the drug content can be granulated with the binder, such as via fluid bed granulation, before the resulting granules are dry blended with the lubricant and the resulting composition is compressed into solid tablets. Other configurations are also possible.

In one embodiment, the binder content is omitted completely, in which case the drug content may be dry blended with the lubricant and the resulting composition may be tableted via direction compression. In such embodiments, the drug content can constitute about 90% to about 97% of the drug content by weight, such as between about 91% and about 96% of the drug content by weight, and in some cases between about 92% and about 95% of the drug content by weight. The lubricant content can comprise a lubricant such as a high molecular weight PEG, and in some cases the lubricant content is primarily or completely formed from PEG alone, such as PEG 8000. Alternatively, the lubricant content can comprise a lubricant such as a leucine, and in some cases the lubricant content is primarily or completely formed from leucine alone.

Figure 11:
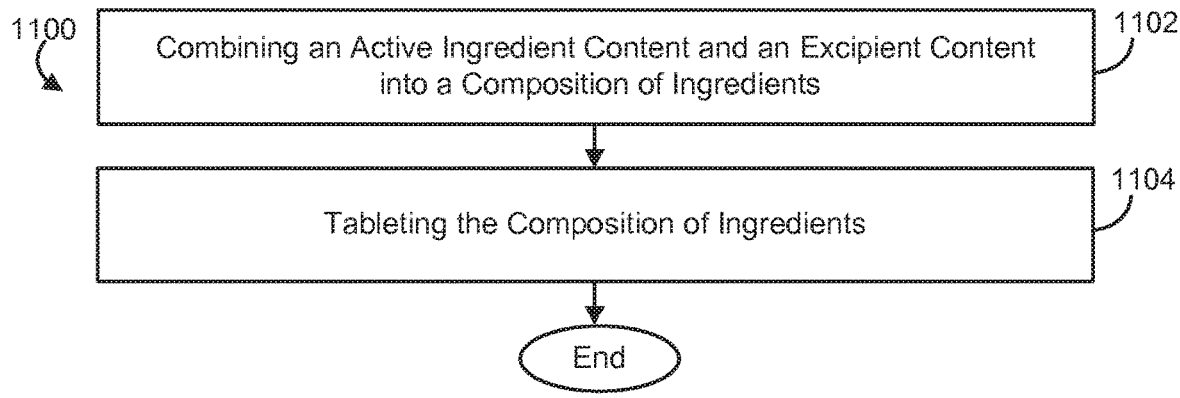
FIG. 11 is a block diagram illustrating an embodiment of a method of making a solid drug tablet.

FIG. 11 is a block diagram illustrating an embodiment of a method 1100 for making a solid drug tablet. In block 1102, a drug content and an excipient content are combined into a composition of ingredients to be tableted. In block 1104, the composition of ingredients is tableted. In embodiments in which the solid drug tablets are designed for use in a drug delivery device of the type described above with reference to FIG. 3, the drug tablets are "mini-tablets" that are suitably sized and shaped for insertion through a natural lumen of the body, such as the urethra, as described above with reference to FIG. 6.

In some embodiments of block 1102, the active ingredient content and the excipient content are directly combined to create the composition of ingredients. The contents can be dry blended using, for example, a V-blender. In other embodiments of block 1102, the composition of ingredients is formed in at least two discrete stages. In a first stage, at least a portion of the active ingredient content is agglomerated into particles of increased size, which are commonly referred to as "granules." The active ingredient content can be agglomerated using any granulation process, such as wet granulation, dry granulation, fluid bed granulation, or a combination thereof, either alone or in the presence of an excipient such as a binder. Granulating the active ingredient content into larger particles reduces its surface area as a whole, which advantageously permits lowering the overall excipient content needed for tableting the composition in block 1104. In a second stage, the granules are combined with any remaining ingredients to form the composition to be tableted. For example, the granules can be blended with lubricants or other excipients using a dry blending process, such as in a V-blender. The resulting composition is then tableted in block 1104.

In embodiments in which the excipient content includes a binder and a lubricant, the binder can be used in the first stage to granulate the active ingredient content into particles of increased size, and the lubricant can be added in the second stage after the granules have been formed. Due to the granulation of the active ingredient content, a relatively smaller quantity of lubricant may be needed, which lowers the overall weight of the excipient content in the final tablet.

In preferred embodiments, at least the drug content and the lubricant content are in the form of dry powders, while the binder content may be a powder or a solution. For example, the drug content can be a powder that is granulated with an aqueous binder using a fluid bed granulation process, and the resulting granules can be dry blended with the lubricant to form the composition to be tableted. Particularly, fluid bed granulation entails pre-blending the active ingredient content in a bed using fluidized air, granulating the active ingredient content by spraying an aqueous binder onto the fluidized powder bed, and then drying the granulated powder to the desired moisture content. However, other granulation processes may be used.

In embodiments in which the active ingredient content comprises lidocaine hydrochloride monohydrate, the active ingredient content may be granulated in a number of different manners. Various studies were performed to investigate methods of increasing the particle size of lidocaine, such as slugging, roller compaction, and fluid bed granulation. The results of these studies are described with reference to Examples 2-4 below. These studies generally show that fluid bed granulation may be particularly suited for granulating an active ingredient such as lidocaine hydrochloride monohydrate powder using an excipient such as an aqueous solution of povidone.

In such embodiments, an aqueous solution of povidone is formed, such as one having a concentration of about 5% w/w to about 15% w/w povidone. Once the lidocaine is in the fluidized bed, the lidocaine may be heated to a target temperature. The target temperature may be in the range of about 30 to about 50° C., such as about 33 to about 37° C. Once the lidocaine has reached the target temperature, the solution can be applied at a spray rate of about 8 to about 15 g/min, such as about 9.0 to about 11.5 g/min. The solution is sprayed until the desired amount of povidone has been added. Granules are formed after drying the resulting combination for a suitable time, such as about 2 minutes.

The resulting composition is then tableted in block 1104. Tableting the composition of ingredients generally comprises compressing the composition of ingredients into a solid tablet. The tableting process is generally known as "direct compression" in cases in which the composition of ingredients has been directly blended in block 1102. Compression also is used to form tablets from compositions formed in stages that include a granulation stage.

In some embodiments of block 1104, tableting the composition of ingredients comprises processing the composition on a tablet machine, such as rotary tablet machine. The tablet machine has a series of dies and punches. The dies receive the composition of ingredients, and the punches are operated with various forces to form the composition of ingredients into solid drug tablets. The size, shape, and hardness of the solid drug tablets are determined by the size and shape of the dies and punches, and the injection and compression forces used to operate the punches.

The solid tablet can be formed in a variety of configurations, but in particular embodiments the tablet is a mini-tablet as described above. To form a mini-tablet, the press table of the rotary tablet machine may be operated with tooling in the range of about 1.0 to about 3.5 mm, such as about 1.3 to about 2.9 mm. In one particular embodiment, 1.5 mm tooling is used, and in another particular embodiment, 2.6 mm tooling is used. The punches may have substantially flat faces for forming flat mini-tablets. Tableting studies were performed using lidocaine. The results of these studies are below in Examples 5-7.

Once the solid drug tablets are formed, the drug tablets may be loaded into the drug delivery device. An example method for loading the tablets is described below with reference to FIG. 13. After the device is loaded, the device preferably is sterilized. The selected sterilization process does not undesirably alter the physical or chemical composition of the solid drug tablets or other components of the device. Examples of suitable sterilization processes include gamma irradiation or ethylene oxide sterilization, although other sterilization processes may be used. For example, gamma irradiation at a strength of about 8 KGy to about 40 KGy, such as about 25 KGy, can be employed.

The drug tablets described above include a relatively higher percentage of active ingredients than excipients. The drug tablets can be formed using a stable and scalable manufacturing process and are suitable for the intended use. Particularly, the drug tablets are sized and shaped for loading into and efficiently storing the tablets in a linear array in an drug delivery device that can be deployed into the bladder or another cavity, lumen, or tissue site in a patient in a minimally invasive manner.

In addition, the drug tablets can be sterilized before or after loading/assembly into a drug delivery device, and the drug tablets possess a commercially reasonable shelf life. Once implanted, the composition of the drug tablets is appropriate for the intended route of administration, is stable in acidic conditions, and provides pre-selected, reproducible drug release kinetics. For example, the drug tablets may be solubilized in the bladder to continuously release drug at a suitably stable rate drug over an extended period.

Although mini-tablets and other solid drug tablets are described above as having a high weight fraction of drug or API and a low weight fraction of excipients, the solid drug tablets may have any weight fraction of drug, especially in cases in which the tablet includes a drug that is extremely potent, a stabilizing agent, or an agent that increases the solubility of the drug, among others or combinations thereof.

III. Method of Making the Device

Figure 12:
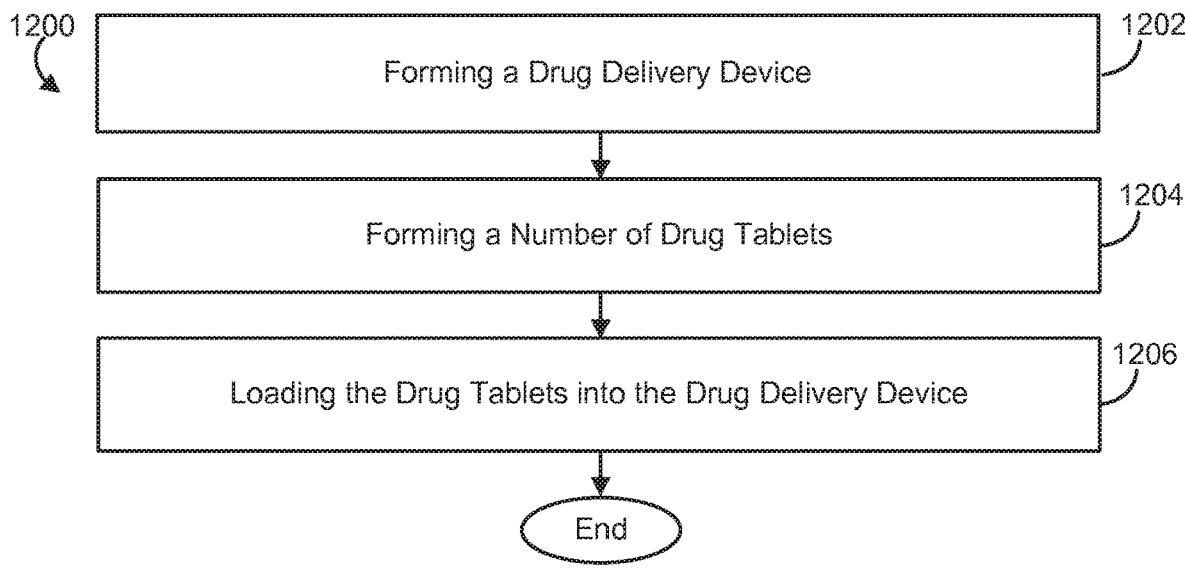
FIG. 12 is a block diagram illustrating an embodiment of a method of making a drug delivery device.

FIG. 12 is a block diagram illustrating an embodiment a method 1200 of making an implantable drug delivery device. In block 1202, a drug delivery device is formed. In block 1204, a number of drug tablets are formed. In block 1206, the drug tablets are loaded into the drug delivery device.

In embodiments, forming the drug delivery device in block 1202 may include one or more of the following sub-steps: forming a device body, forming a retention frame, associating the device body with the retention frame, and forming one or more apertures in the device body.

Forming the device body may include forming a flexible body having walls that define a drug reservoir lumen and a retention frame lumen. For example, the device body may be formed by extruding or molding a polymer such as silicone. In particular, forming the device body may include integrally forming two tubes or walls that are substantially aligned and adjoined along a longitudinal edge. Alternatively, the two lumens may be separately formed and attached to each other, such as with an adhesive. Other methods of forming the device body also may be employed.

Forming a retention frame may include forming an elastic wire from, for example, a superelastic alloy or shape-memory material and "programming" the elastic wire to naturally assume a relatively expanded shape. Heat treatment may be used to program the elastic wire to assume the expanded shape. For example, the retention frame may be formed by forming the elastic wire into a pretzel shape and heat treating the elastic wire at a temperature over 500° C. for a period over five minutes.

Associating the device body with the retention frame may comprise inserting the retention frame into the retention frame lumen of the device body. In some embodiments, a distal end of the retention frame is blunted or is covered in a smooth ball of increased cross section during insertion of the retention frame into the lumen. The ball may facilitate driving the retention frame through the retention frame lumen without puncturing the wall of the device body. Also in some embodiments, the device body may be slightly compressed between two surfaces during the insertion of the retention frame. Compressing the device body elongates the opening into the retention frame lumen, facilitating loading.

In some embodiments, associating the device body with the retention frame further includes filling the retention frame lumen with a filling material after the retention frame is loaded. The filling material occupies the remainder of the lumen not occupied by the retention frame, reducing the ability of the device body to stretch along, or twist or rotate about, the retention frame. For example, silicone or another polymer may be injected or poured into the retention frame lumen and may cure therein. In other embodiments, associating the device body with the retention frame portion may comprise integrally forming the two portions together, such as by overmolding the device body about the retention frame.

Forming one or more apertures in the device body may include laser drilling or mechanically punching one or more holes in the device body. The apertures also may be formed simultaneously with the device body, such as by molding with an indenter as described in U.S. Pat. No. 6,808,522 to Richards et al.

In block 1204, the drug tablets are formed using an embodiment of the method 1100 described above with reference to FIG. 11, although other drug tablet forming methods may be used.

In block 1206, the drug tablets are loaded into the drug delivery device using an embodiment of the method 1300 described below with reference to FIG. 13. Other methods of loading drug tablets also may be used. Embodiments of systems of loading solid drugs are described below with reference to FIGS. 14-15.

Some of the steps and sub-steps of the blocks 1202, 1204, and 1206 may be performed in other orders or simultaneously. For example, the retention frame may be associated with the device body in block 1202 either before or after the drug units are loaded into the device body block in 1206. Similarly, the apertures may be formed in the device body in block 1202 either before or after the drug tablets are loaded in block 1206.

In embodiments, the method 1200 may further include partitioning the drug reservoir lumen into multiple discrete drug reservoirs, such as by positioning one or more partition structures within the drug reservoir lumen in an alternating fashion with the loading of the drug tablets in block 1206. In embodiments, the method 1200 may further include sealing the drug tablets in the device body. The method 1200 may also include associating one or more release controlling structures with the drug reservoir lumen, such as a sheath or coating placed over at least a portion of the surface of the device body to control the rate of release of the drug or a degradable membrane positioned over or in one or more of the apertures to control the initial time of release of the drug therethrough.

Figure 13:
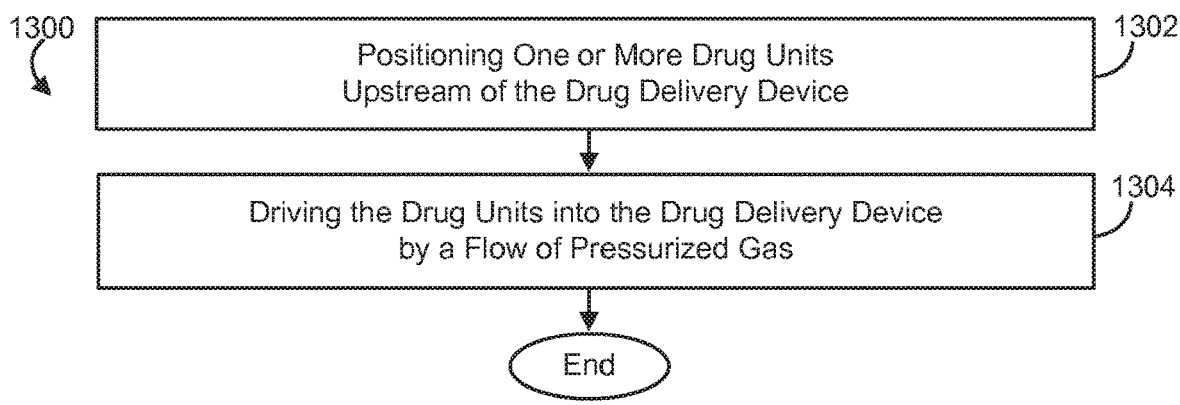
FIG. 13 is a block diagram illustrating an embodiment of a method of loading a drug delivery device with drug units.

FIG. 13 is a block diagram illustrating an embodiment of a method 1300 of loading a drug delivery device with drug units. The method 1300 may load an embodiment of the drug delivery device described herein with embodiments of the drug units described herein, although other drug delivery devices or other drug units may be loaded. The drug delivery device generally includes an entry and an exit. For example, the drug delivery device may be a flexible lumen, the entry may be an opening into the flexible lumen, and the exit may be an opening from the flexible lumen.

In block 1302, one or more drug units are positioned upstream of the drug delivery device adjacent to its entry, such as an opening into a flexible lumen. Positioning the drug units also may include orienting the drug units to enter the drug delivery device and travel along a length of the drug delivery device. For example, the drug units may be oriented in a line or a row adjacent to the entry, either with automatic feeding and orienting equipment, with a push rod, or manually. Positioning the drug units may comprise positioning the drug units between the entry and a pressurized gas source, such as by positioning the pressurized gas source upstream of the drug units. The pressurized gas source may be a conventional syringe filled with air or any other embodiment of a gas source described herein.

In block 1304, the drug units are driven into the drug delivery device by a flow of pressurized gas. Driving the drug units into the drug delivery device may comprise operating a pressurized gas source of the type described herein. The pressurized gas source may provide a flow of gas at positive pressure. The flow of gas may push the drug units into the drug delivery device. For example, the pressurized gas source may be a simple syringe filled with air that is depressed to provide a flow of air into the drug delivery device. In some embodiments, the flow of pressurized gas may slightly expand the drug delivery device to ease the process of loading the drug units. In cases in which the drug units are aligned in the channel of a holder positioned adjacent to the entry of the drug delivery device, driving the drug units into the drug delivery device may comprise directing gas from the pressurized gas source into the holder so that the gas drives the drug units from the holder through the entry. Driving the drug units into the drug delivery device also may include operating a vacuum source. The vacuum source may apply a negative pressure to a volume of gas in the drug delivery device, which may pull the drug units into the drug delivery device. The drug units may be both pushed into the device by a flow of gas at positive pressure and pulled into the device by a flow of gas at negative pressure. Driving the drug units into the drug delivery device also may include blocking at least one orifice of the drug delivery device. Blocking an orifice may impede the flow of pressurized gas from escaping through the orifice. Driving the drug units into the drug delivery device may further include stopping the drug units. For example, the drug units may be stopped using an embodiment of a stopper described above.

Blocks 1302 and 1304 may be performed in other orders. For example, the drug delivery device may be loaded in batches, in which case blocks 1302 and 1304 may be alternated and repeated. The total dose of drug units may be divided into at least two groups, a first group being positioned next to the drug delivery device in block 1302 and loaded into the drug delivery device in block 1304 before the second group is so positioned and loaded. Still other processes are possible within the scope of the present disclosure.

In certain embodiments, the method 1300 further includes blocking entry and exit apertures in the device to impede the drug units from escaping intact from the drug delivery device. The blocking also impedes external agents, such as fluid in the bladder, from entering the drug delivery device through the entry and exit. In such embodiments, blocking the entry and exit may include inserting a plug or other object into the entry and the exit. Inserting the plug may include stretching the entry or exit of the drug delivery device about a plug having a relatively larger diameter or other outer dimension than an inner diameter or dimension of the drug delivery device, so that the plug substantially fills the entry or exit and is snugly retained in position. In embodiments in which the entry and exit are blocked, the drug units may be loaded in blocks 1302 and 1304 before the entry and exits are blocked. However, other sequences are possible. For example, the exit may be blocked once the drug units have been loaded downstream of an orifice in the drug delivery device, as the orifice may provide an escape route for the gas once the exit has been blocked.

Figure 14:
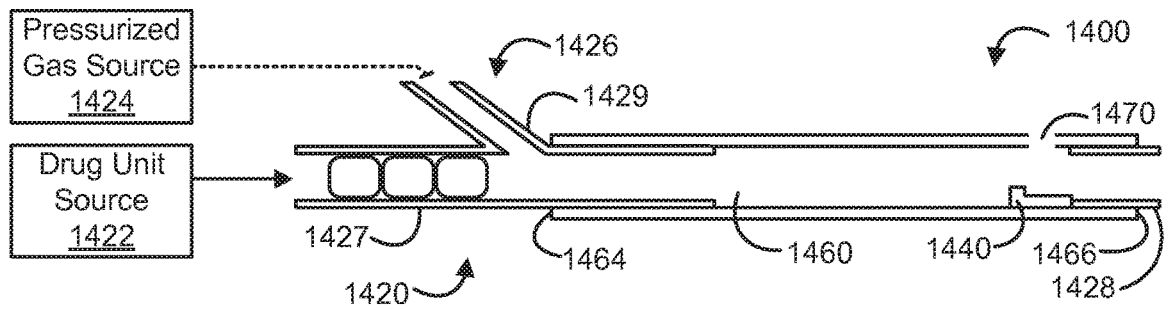
FIG. 14 is a side view of an embodiment of a system for loading a drug delivery device with drug tablets.
Figure 14:
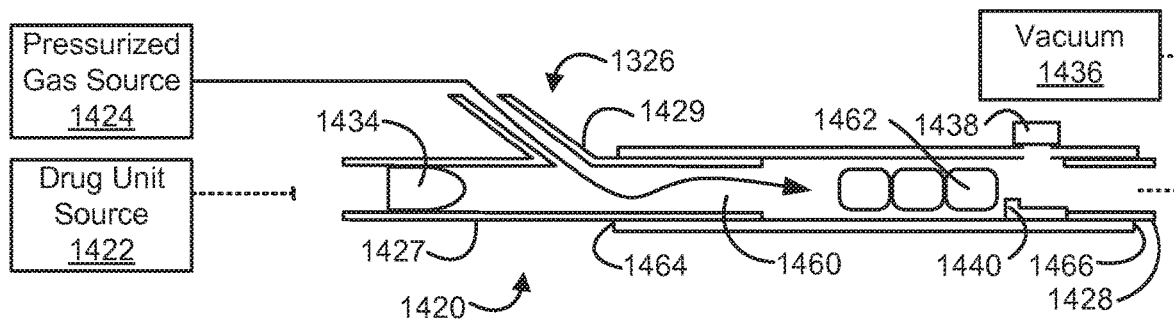

FIG. 14 is a side view of an embodiment of a system 1400 for loading a drug delivery device with one or more drug tablets or other drug units. The system 1400 may include a device holder 1420, a drug unit source 1422, and a pressurized gas source 1424. The system 1400 may be used to load the drug reservoir lumen 1460 of the drug delivery device with drug units 1462, although other drug delivery devices may be loaded. For simplicity, FIG. 14 does not show the retention frame portion of the drug delivery device.

The device holder 1420 may hold the drug reservoir lumen 1460 in a suitable orientation for loading. An example device holder 1420 may include an entry channel 1426 mounted to the entry 1464 of the drug reservoir lumen 1460 and an exit channel 1428 mounted to the exit 1466 of the drug reservoir lumen 1460. The drug unit source 1422 may retain one or more drug units 1462 prior to loading.

Examples include a cartridge, a cassette, a storage bin, a hopper, or combinations of these and other storage devices. The pressurized gas source 1424 may provide a flow of gas at a suitable pressure to drive the drug units 1462 into the drug reservoir lumen 1460. Example pressurized gas sources 1424 may include a device that supplies a pressurized flow of inert gas such as nitrogen or argon, or a device suited for pressurizing ambient air such as a compressor. A simple syringe filled with air also may be used.

The entry channel 1426 may include a drug inlet portion 1427 and an air inlet portion 1429 as shown. The drug inlet portion 1427 may be in communication with the drug unit source 1422 and the air inlet portion 1429 may be in communication with the pressurized gas source 1424. The air inlet portion 1429 may be angled relative to the device lumen to facilitate the flow of pressurized gas into the entry channel 1426. However, two inlet portions need not be provided.

A downstream end of the entry channel 1426 may be coupled to the entry 1464 of the drug reservoir lumen 1460, so that drug units 1462 may be loaded into the drug reservoir lumen 1460 under a flow of pressurized gas. The exit channel 1428 may be coupled to the exit 1468 of the drug reservoir lumen 1460, so that the flow of pressurized gas may be communicated from the drug reservoir lumen 1460 after the drug units 1462 are loaded.

Before the drug units 1462 are loaded in the drug delivery device, the drug units 1462 may be moved from the drug unit source 1422 into the downstream portion of the entry channel 1426, so that the drug units 1462 are adjacent to the entry 1464 of the drug reservoir lumen 1460. Specifically, the drug units 1462 may be moved downstream from the air inlet 1429. The drug units 1462 may be manually moved downstream of the air inlet 1429, such as using a push rod or the force of gravity as shown, or the process may be at least partially automated as described below with reference to FIG. 15.

Regardless, the drug units 1462 may become positioned to enter the drug reservoir lumen 1460. The drug units 1462 may be aligned serially, with each drug unit 1462 in a suitable orientation for passing into the drug reservoir lumen 1460. For example, a cylindrical outer surface of each drug unit 1462 may be oriented to contact an cylindrical inner surface of the drug reservoir lumen 1460, and planar end faces of the drug units 1462 may be oriented to contact planar end faces of adjacent drug units 1462. The drug units 1462 may be manually reoriented in a suitable orientation, or the process of orienting the drug units 1462 may be automated, such as described below with reference to FIG. 15.

The pressurized gas source 1424 may be positioned upstream of the drug units 1462 in the entry channel 1426. For example, the air inlet portion 1429 may be located at a distance from the entry 1464 to the drug reservoir lumen 1460. The distance may be sufficient to ensure the flow of pressurized gas is applied upstream of the drug units 1462 when the drug units 1462 are positioned in the entry channel 1426. The distance may be selected based on, for example, the number of drug units 1462 to be loaded and the length of each drug unit 1462. Thus, the drug units 1462 may be positioned between the air inlet 1429 and the entry 1464 to the drug reservoir lumen 1460, so that when the pressurized gas source 1424 is operated, a flow of pressurized gas drives the drug units 1462 into the drug reservoir lumen 1460.

A plug 1434 may be positioned in the drug inlet portion 1427 before the pressurized gas source 1424 is operated. The plug 1434 may prevent the flow of pressurized air from traveling backward through the drug inlet portion 1427, ensuring the flow of pressurized air is directed through the entry channel 1426 to drive the drug units 1462 into the drug reservoir lumen 1460.

The pressure employed by the pressurized gas source 1424 is sufficient to drive the drug units 1462 into the drug delivery device. For example, the pressure may be selected based on factors such as the size and shape of the drug reservoir lumen 1460, the material used to form the drug reservoir lumen 1460, the size, shape, weight, and content of the drug units 1462, the number of drug units 1462 to be driven into the drug reservoir lumen 1460 at a time, the length of the drug reservoir lumen 1460 through which the drug units 1462 travel, and the number and positioning of orifices 1470 along the drug reservoir lumen 1460, among other factors or combinations thereof. The pressure may be sufficient to cause the drug reservoir lumen 1460 to circumferentially expand. Thus, the flow of pressurized gas may travel about outer peripheries of the drug units 1462, so that the gas is able to exit the drug reservoir lumen 1460 into the exit channel 1428. Also, drug units 1462 that have a relatively larger diameter than the drug reservoir lumen 1460 may be loaded, and the drug reservoir lumen 1460 may return after the pressurized gas flow abates to snugly retain the drug units 1462.

In one embodiment, an inner surface of the drug reservoir lumen 1460 is provided with a powder coating, such as microparticles of the drug, an excipient agent, or a combination thereof. The powder coating may act as a lubricant that decreases friction between the drug units 1462 and the inner surface of the drug reservoir lumen 1460. In such embodiments, the pressurized gas source 1424 may be operated at a reduced pressure. The powder coating may be supplied by pre-treating the drug reservoir lumen 1460 or from slight disintegration of drug units 1462 traveling through the drug reservoir lumen 1460. The powder coating may be filtered at the exit channel 1428.

In one embodiment, the pressurized gas source 1424 is operably associated with one or more filters. For example, an upstream filter may filter the flow of pressurized gas entering the drug delivery device, such as to remove any contaminants that may interact with the drug units 1462. As another example, a downstream filter may filter the flow of pressurized gas exiting the drug delivery device, such as in cases in which powderized drug and/or excipients may be present in the gas.

The pressurized gas source 1424 also may include a vacuum 1436. The vacuum 1436 may be positioned downstream of the exit channel 1428 in communication with the exit 1468 of the drug reservoir lumen 1460. The vacuum 1436 may apply a negative pressure that draws the flow of pressurized gas from the exit 1468 to further assist the loading process. However, the vacuum 1436 is not necessary and may be omitted, or the vacuum 1436 may be provided alone, in which case the pressurized gas source 1424 may not supply a flow of pressurized gas at positive pressure to the entry 1464 of the drug reservoir lumen 1460.

In one embodiment, the system 1400 also includes an orifice blocker 1438. The orifice blocker 1438 may be positioned adjacent to or in the orifice 1470 to block the flow of pressurized gas from escaping. The use of the orifice blocker 1440 may be helpful in cases in which the orifice 1470 is located about the entry 1464 or an intermediate section of the drug reservoir lumen 1460. In such cases, the flow of pressurized gas may be inclined to escape through the orifice 1470, such as once some of the drug units 1462 become positioned at the exit 1466 of the drug reservoir lumen 1460. The orifice blocker 1438 may be omitted in cases in which the orifice 1470 is located adjacent to the exit 1466, or in cases in which the drug units 1462 have been loaded to a position past the orifice 1470.

In one embodiment, the system 1400 also includes a stopper 1440. The stopper 1440 may assist with stopping the drug units 1462 within the drug reservoir lumen 1460. For example, the stopper 1440 may engage a first drug unit 1462 to apply a stopping force to the first drug unit 1462. Thus, the first drug unit 1462 may be stopped at a selected axial position, such as adjacent to the exit 1466 from the drug reservoir lumen 1460. In turn, subsequent drug units 1462 may be stopped by the preceding drug units 1462 that are no longer in motion.

The configuration of the stopper 1440 may be selected to apply an adequate stopping force to the first drug unit 1462 without damaging it. For example, the stopper 1440 may have a sufficient contact area and rigidity. In particular, the contact area of the stopper 1440 may be sized and shaped to prevent the first drug unit 1462 from traveling forward while permitting the flow of pressurized gas to continue traveling out of the drug reservoir lumen 1460.

For example, the embodiment of the stopper 1440 shown in FIG. 14 includes a leg that axially extends from the exit channel 1428 into the drug reservoir lumen 1460, and a foot that protrudes upward from a distal end of the leg. The foot may apply a stopping force to the first drug unit 1462 as it travels through the drug reservoir lumen 1460. The contact area of the foot may be large enough to stop the first drug unit 1462 without completely blocking the drug reservoir lumen 1460, so that the pressurized air flow may continue past the foot and into the exit channel 1428.

The stopper 1440 also may be formed by an end surface of the exit channel 1428, which may have a surface area that contacts the first drug unit to prevent continued forward movement. The surface area of the end surface 1442 may be increased by partially enclosing the exit channel 1428, which may increase the contact area available for stopping the first drug unit. In some embodiments, the end surface may include one or more cut outs or channels, which permit the flow of pressurized gas to travel past the drug units 1462 and out of the drug reservoir lumen 1460. The exit channel 1428 also may have a porous end portion, which may act as a stopper 1440 and as a filter, such that drug powder debris exiting the drug reservoir lumen 1460 is removed. In still other embodiments, the stopper 1440 may be a thin wire having a diameter that is relatively smaller than an inner diameter of the drug reservoir lumen 1460, which may facilitate inserting the thin wire along the length of the drug reservoir lumen 1460. Thus, the thin wire may facilitate stopping the first drug unit 1462 about an intermediate section of the drug reservoir lumen 1460 without impeding the flow of pressurized air toward the exit 2908. On the other hand, the thin wire may have a diameter that is large enough to provide an end face with sufficient contact area for stopping the first drug unit without imparting a damaging force or a rotating moment on the first drug unit. It should be noted that the stopper 1440 may have a combination of these and other configurations in other embodiments.

Figure 15:
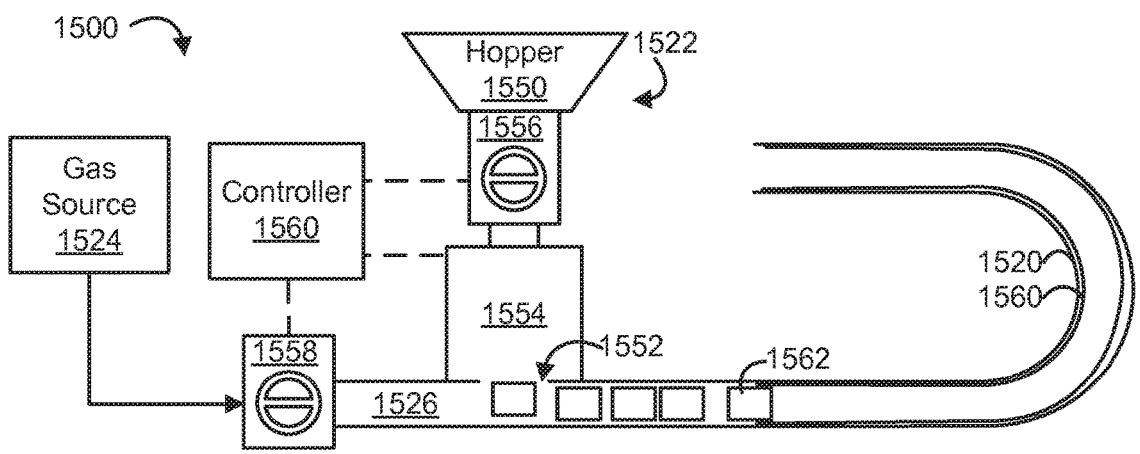
FIG. 15 is a schematic of another embodiment of a system for loading a drug delivery device with drug units.

FIG. 15 is a side view of another embodiment of a system 1500 for loading a drug delivery device 1560 with drug units 1562. Like the system 1400, the system 1500 may include a device holder 1520, a drug unit source 1522, and a pressurized gas source 1524.

As described above, the device holder 1520 may hold the drug delivery device 1560 during the loading process. In embodiments, the device holder 1520 may be configured to hold the drug delivery device 1560 in a selected shape. For example, the device holder 1520 may have a curvature as shown. Such a device holder 1520 may be useful in cases in which the drug delivery device 1560 includes an elastic wire that is preconfigured to spontaneously return to a retention shape, such as a pretzel shape. The curvature of the device holder 1520 may hold the device 1560 in a partially curled state, which may permit the device 1560 to be loaded without completely uncurling the elastic wire. For simplicity, the elastic wire is not shown.

The drug unit source 1522 may be a drug receptacle or bin, such as a hopper 1550. The drug unit source 1522 may be in communication with a drug entry opening 1552 into an entry channel 1526 of the device holder 1520. The drug unit source 1522 may be upstream from the drug entry opening 1552, such that drug units 1562 may be directed into the entry channel 1526 at the drug entry opening 1552. The hopper 1550 may employ the force of gravity to direct drug units 1562 through the drug entry opening 1552. For example, the hopper 1550 may have a funnel shape and may be positioned above the drug entry opening 1552. Alternatively or additionally, the hopper 1550 may employ an external force to direct the drug units 1562 through the drug entry opening 1552.

In some embodiments, an orienting apparatus 1554 is positioned between the drug unit source 1522 and the drug entry opening 1552. The orienting apparatus 1554 may be any pharmaceutical or other materials handling equipment suited to serialize and orient the drug units 1562 into an appropriate orientation for passing into the drug delivery device 1520. Example orienting apparatuses may include a vibratory feeder, a gravity feeder, a centrifugal feeder, an inline feeder, tracks, or guide rails, among others or combinations thereof.

In some embodiments, the drug unit source 1522 is associated with a drug unit source valve 1556. The drug unit source valve 1556 may be positioned between the drug unit source 1522 and the drug entry opening 1552. The drug unit source valve 1556 may selectively permit or prevent the passage of drug units 1562 through the drug entry opening 1552.

The pressurized gas source 1524 may have any of the configurations described above, among other configurations. In some embodiments, the pressurized gas source 1524 is in communication with the entry channel 1526 from a point upstream of the drug entry opening 1552 and provides a flow of pressurized gas at a positive pressure. In some embodiments, the pressurized gas source 1524 is associated with a pressurized gas source valve 1558. The pressurized gas source valve 1558 may be positioned upstream of the drug entry opening 1552. The pressurized gas source valve 1558 may selectively permit or prevent the flow of pressurized gas through the entry channel 1526. The pressurized gas source 1154 also may include a vacuum positioned downstream that applies a negative pressure.

In preferred embodiments, the system 1500 includes a controller 1560. The controller 1560 may be operable to control the drug unit source valve 1556 and the pressurized gas source valve 1558 to facilitate loading the drug units 1562. For example, the valves 1556, 1558 may be opened and closed in a manner that prevents the flow of pressurized gas when the flow of drug units 1562 is permitted, and alternatively permits the flow of pressurized gas when the flow of drug units 1562 is prevented. The valves 1556, 1558 may be alternated between opened and closed positions in opposite, with an appropriate time delay as needed to compensate for delays in the system 1500 or the geometry of the system 1500, among others or combinations thereof.

In another embodiment, the controller 1560 also is operable to control the pressurized gas source 1524 directly. In such embodiments, the controller 1560 causes the pressurized gas source 1524 to provide, or prevents the pressurized gas source 1524 from providing, the flow of pressurized gas. In such embodiments, the pressurized gas source valve 1558 may or may not be provided. In embodiments in which the pressurized gas source 1524 includes a vacuum, the controller 1560 also may control the vacuum. The controller 1560 may be operable to control the drug unit source 1522 and/or the orienting apparatus 1554, in whole or in part.

Figure 16:
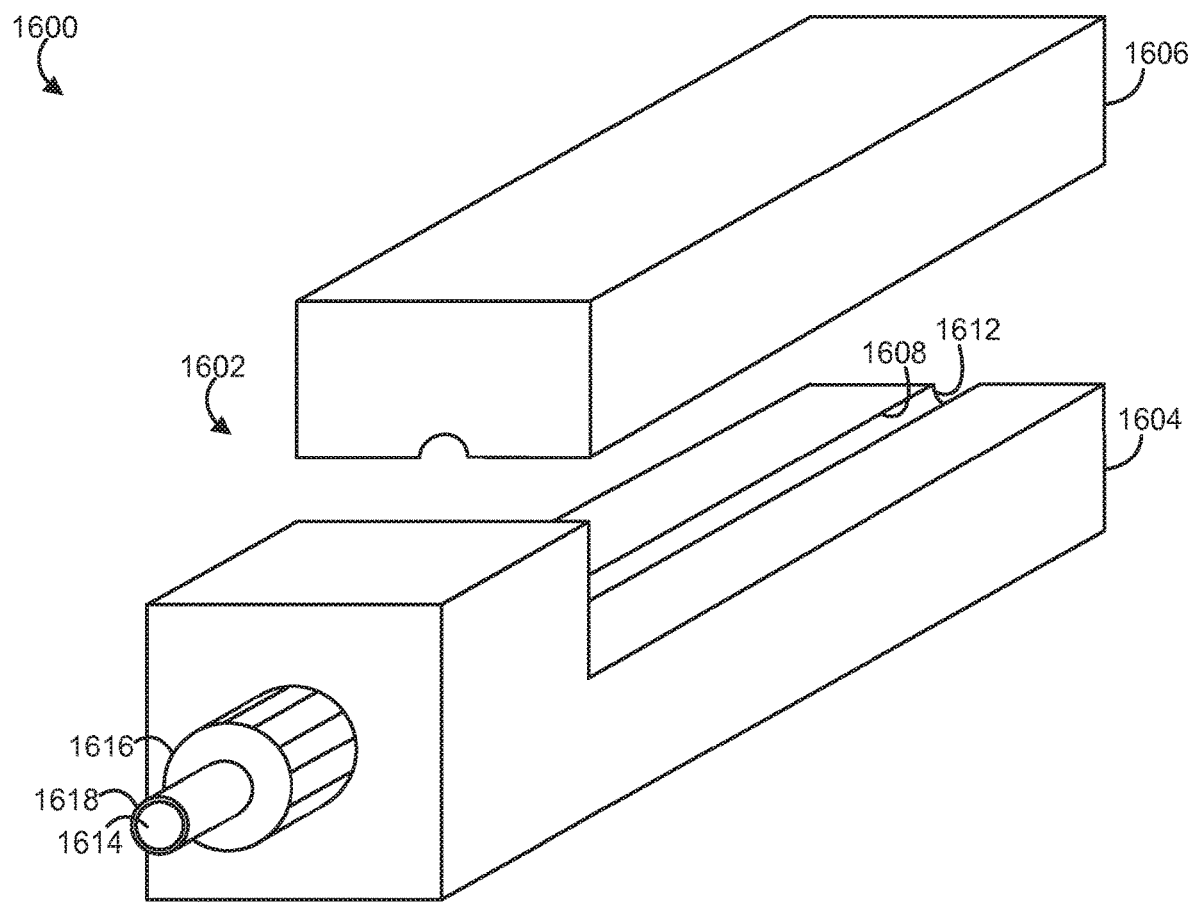
FIG. 16 is a perspective view of another embodiment of a system for loading a drug delivery device with drug units.
Figure 17:
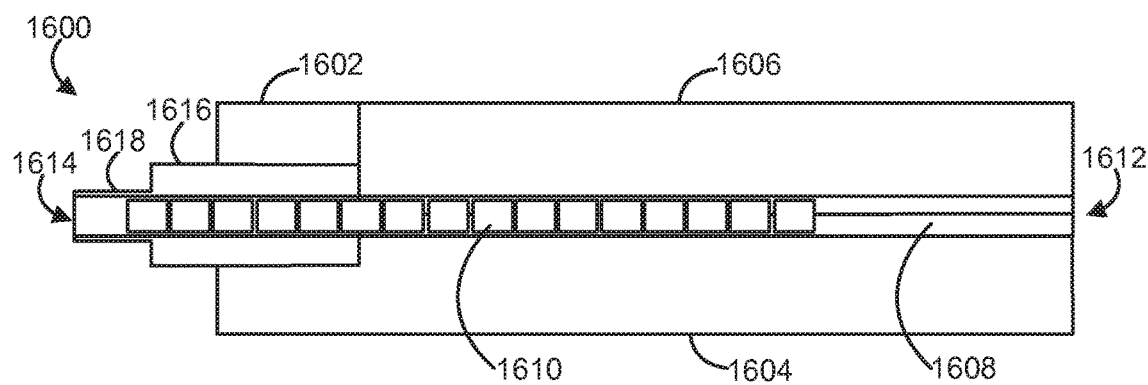
FIG. 17 is a cross-sectional view of the embodiment of the system for loading a drug delivery device shown in FIG. 16.

FIGS. 16 and 17 illustrate another embodiment of a system 1600 for loading a drug delivery device with drug units. The system 1600 generally includes a holder 1602 formed from a base portion 1604 and a cover portion 1606. Together, the base and cover portions 1604, 1606 define a channel 1608 for receiving a number of drug tablets 1610. The channel 1608 may be shaped to hold a number of drug units 1610 that are serially aligned. For example, the channel 1608 may be a straight line as shown, or the channel 1608 may curve. The channel 1610 may have a cross-section that is slightly larger than the drug tablets 1610 so that the drug tablets 1610 can fit completely within the channel 1608 in a serially arrangement.

The cover portion 1606 may be removable so that the base and cover portions 1604, 1606 can be separated to load the channel 1608 with drug tablets 1610. The cover portion 1606 also may be releasably securable to the base portion 1604 so that the drug tablets 1610 can be secured in the channel 1608 once loaded. For example, the cover portion 1606 may be associated with a number of screws that can engage threaded openings in the base portion 1604, or the cover portion 1606 may be associated with a number of clamps that can clamp to the base portion 1604. Other configurations are also possible.

When the base and cover portions 1604, 1606 are secured together, the channel 1608 is relatively enclosed except for an entry 1612 located at the rear of the holder 1602 and an exit 1614 located at the front of the holder 1602. In operation, the entry 1612 may be associated with a source of pressurized gas and the exit 1614 may be associated with an entry opening into the drug delivery device. When the source of pressurized gas is operated, the gas may travel through the channel 1608 to drive the drug tablets 1610 through the exit 1614 of the holder and into the entry opening in the drug delivery device.

Any source of pressurized gas may be used. In particular embodiments, the source of pressurized gas is a syringe of air associated with the entry 1612 of the holder 1600. A tip of the syringe may be inserted into the entry 1612, and the syringe may be depressed to expel air into the channel 1608, driving the drug units 1610 forward. Thereby, the drug delivery device may be loaded.

In some embodiments, the holder 1602 further includes a nozzle 1616 that facilitates placing the channel 1608 of the holder 1600 in communication with the entry opening into the drug delivery device. The nozzle 1616 may be located on the front of the holder 1600. The nozzle 1616 is generally sized to correspond to the drug delivery device so that the device can be placed about the nozzle 1616. In some embodiments, an outer surface of the nozzle 1616 is shaped to create a friction fit with drug delivery device, facilitating retention of the device on the nozzle 1616. For example, the nozzle 1616 may be ridged, furrowed, corrugated, or otherwise roughened. The nozzle 1616 may have a tip portion 1618 of reduced cross-section, which is suited for guiding the nozzle 1616 into the entry opening of the drug delivery device. The tip portion 1618 may terminate in the exit 1614, and the channel 1608 may extend form the exit 1614 through the tip portion 1618 and remainder of the nozzle 1616 to the base and cover portions 1604, 1606. When the source of pressurized gas is operated, the drug tablets 1610 may be driven along the channel 1608 through the nozzle 1616 and from the exit 1614 in the tip portion 1618 into the drug delivery device. For simplicity, neither the drug delivery device nor the pressurized gas source is shown in the figures.

Embodiments of the systems and methods described above facilitate loading drug delivery devices with drug tablets or other drug units in a solid form. Because the drug is substantially solid, a larger amount of drug may be fit in a relatively smaller space, which may permit reducing the size of an implantable device that delivers a selected payload, increasing the payload that may be delivered from a device of a selected size, or a combination thereof. The increased payload and/or decreased size of the device may be achieved without sacrificing device flexibility, which may permit configuring the device between a low-profile shape suited for insertion through a deployment positioned in a lumen of the body, such as through the urethra, and a high-profile shape suited for retention in a cavity of the body. The systems and methods may permit loading the device with multiple drug units at a given time in a manner that is relatively quick, efficient, and repeatable. For example, the loading process may be substantially automated in some cases.

IV. Use and Applications of the Device

The device may be implanted in a body cavity or lumen, and subsequently may release one or more drugs for the treatment of one or more conditions, locally to one or more tissues at the deployment site and/or regionally to other tissues distal from the deployment site. The release may be controlled over an extended period. Thereafter, the device may be removed, resorbed, or excreted.

Figure 18:
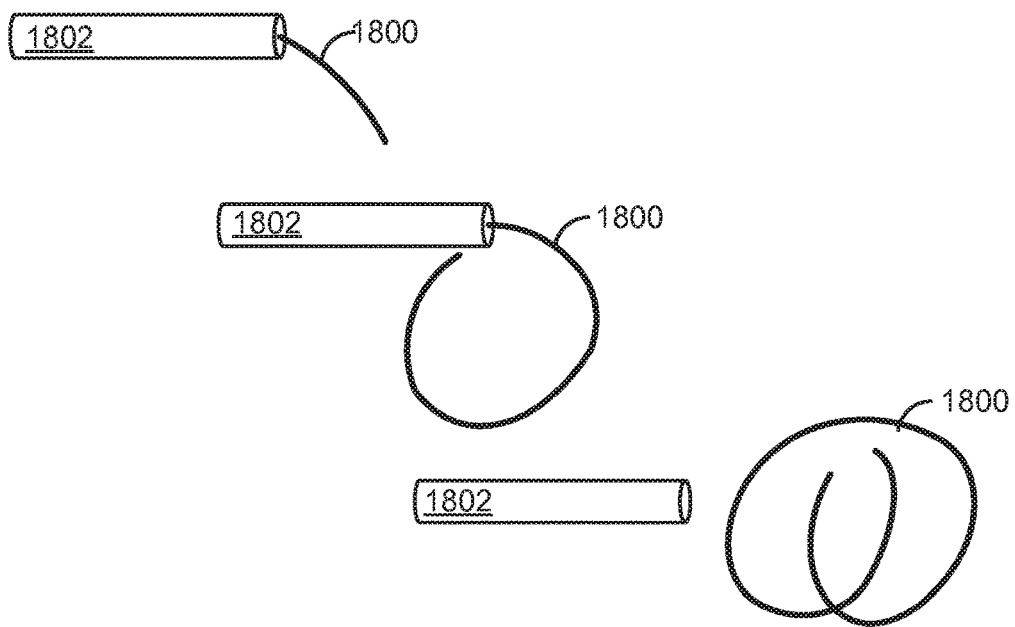
FIG. 18 illustrates a method of implanting a drug delivery device.

In one example, the device is implanted by passing the drug delivery device through a deployment instrument and releasing the device from the deployment instrument into the body. In cases in which the device is deployed into a body cavity such as the bladder, the device assumes a retention shape, such as an expanded or higher profile shape, once the device emerges from the deployment instrument into the cavity. An example is illustrated in FIG. 18, which shows the device 1800 assuming a retention shape as the device exits a deployment instrument 1802. The deployment instrument 1802 may be any suitable lumen device, such as a catheter, urethral catheter, or cystoscope. These terms are used interchangeably herein, unless otherwise expressly indicated. The deployment instrument 1802 may be a commercially available device or a device specially adapted for the present drug delivery devices.

Once implanted, the device may release the drug. The device may provide extended, continuous, intermittent, or periodic release of a desired quantity of drug over a desired, predetermined time period. In embodiments, the device can deliver the desired dose of drug over an extended period, such as 12 hours, 24 hours, 5 days, 7 days, 10 days, 14 days, or 20, 25, 30, 45, 60, or 90 days, or more. The rate of delivery and dosage of the drug can be selected depending upon the drug being delivered and the disease or condition being treated.

In embodiments in which the device comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure. For example, the drug may be solubilized upon contact with urine in cases in which the device is implanted in the bladder.

Subsequently, the device may be retrieved from the body, such as in cases in which the device is non-resorbable or otherwise needs to be removed. Retrieval devices for this purpose are known in the art or can be specially produced. The device also may be completely or partially bioresorbable, such that retrieval is unnecessary, as either the entire device is resorbed or the device sufficiently degrades for expulsion from the bladder during urination. The device may not be retrieved or resorbed until some of the drug, or preferably most or all of the drug, has been released. If needed, a new drug-loaded device may subsequently be implanted, during the same procedure as the retrieval or at a later time.

Figure 19:
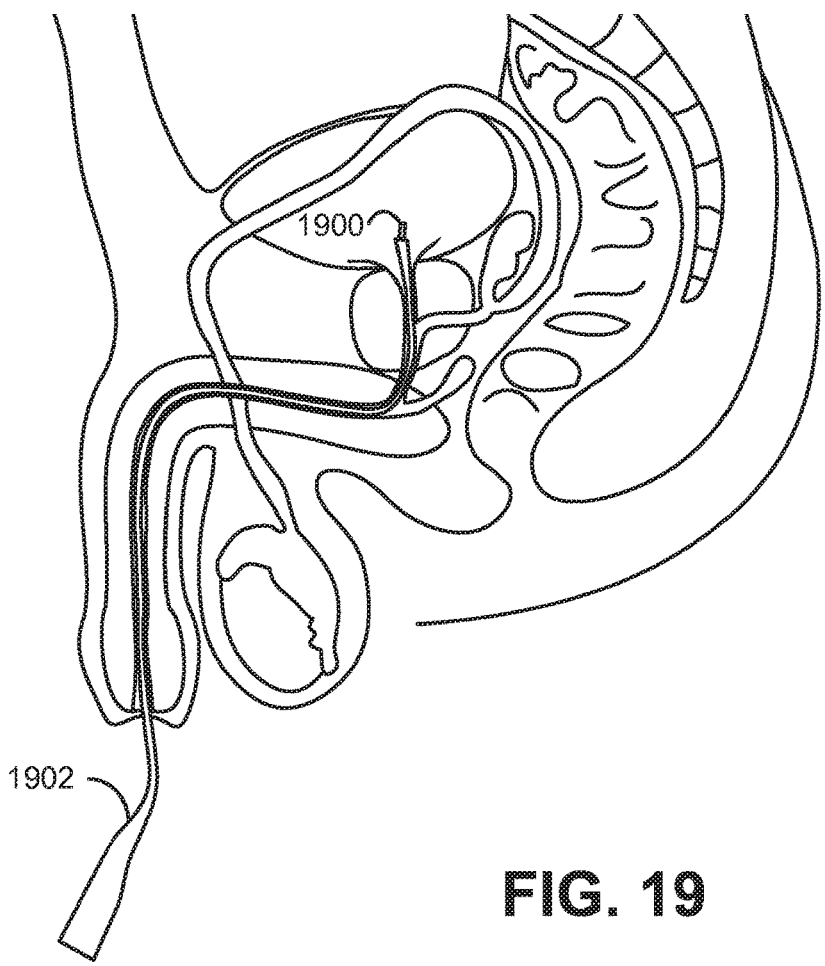
FIG. 19 is a sagittal view of a male patient, illustrating a drug delivery device exiting a deployment instrument into a bladder of the patient.

FIG. 19 illustrates the implantation of a device 1900 into the bladder, wherein the adult male anatomy is shown by way of example. A deployment instrument 1902 may be inserted through the urethra to the bladder, and the device 1900 may be passed through the deployment instrument 1902, driven by a stylet or flow of lubricant or other fluid, for example, until the device 1900 exits into the bladder. Thus, the device is implanted into the bladder of a male or female human patient in need of treatment, either adult or child.

The device may be deployed into the bladder of a patient in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

In one embodiment, the implantable device, with a self-contained drug payload, is deployed wholly within the bladder to provide local, sustained delivery of at least one drug locally to the bladder in an effective amount. Following in vivo deployment of the device, at least a portion of the payload of drug is released from the device substantially continually over an extended period, to the urothelium and possibly to nearby tissues, in an amount effective to provide treatment or to improve bladder function in the patient. In a preferred embodiment, the device resides in the bladder releasing the drug over a predetermined period, such as two weeks, three weeks, four weeks, a month, or more.

In such cases, the device may be used to treat interstitial cystitis, radiation cystitis, pelvic pain, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may deliver drugs that improve bladder function, such as bladder capacity, compliance, and/or frequency of uninhibited contractions, that reduce pain and discomfort in the bladder or other nearby areas, or that have other effects, or combinations thereof. The bladder-deployed device also may deliver a therapeutically effective amount of one or more drugs to other genitourinary sites within the body, such as other locations within urological or reproductive systems of the body, including one or both of the kidneys, the urethra, one or both of the ureters, the penis, the testes, one or both of the seminal vesicles, one or both of the vas deferens, one or both of the ejaculatory ducts, the prostate, the vagina, the uterus, one or both of the ovaries, or one or both of the fallopian tubes, among others or combinations thereof. For example, the intravesical drug delivery device may be used in the treatment of kidney stones or fibrosis, erectile dysfunction, among other diseases, disorders, and conditions.

In some embodiments, the intravesical drug delivery device is deployed into the bladder of a patient for regional drug delivery to one or more nearby genitourinary sites. The device may release drug locally to the bladder and regionally to other sites near the bladder. Such delivery may provide an alternative to systemic administration, which may entail undesirable side effects or result in insufficient bioavailability of the drug.

In one embodiment, the intravesical drug delivery device is implanted into a bladder to locally deliver a local anesthetic agent for management of pain arising from any source, such as a disease or disorder in genitourinary tissues, or pain stemming from any bladder procedure, such as surgery, catheterization, ablation, medical device implantation, or stone or foreign object removal, among others. For example, a local anesthetic agent can be released into the bladder for regional delivery to nearby sites to manage nearby pain arising from any source, such as post-operative pain associated with the passage of a medical device into or through a ureter or other post-operative pain in sites apart from the bladder.

In one particular embodiment, a device having a payload of lidocaine may be delivered to the bladder, and lidocaine may be continuously released from the device over an extended period. In one embodiment, local delivery of lidocaine to the urothelium of the bladder is provided from the presently disclosed devices which have been deployed into the bladder in a manner which achieves a sustained level of lidocaine above the concentration that could be obtained for an extended period via instillation, yet without the high initial peak observed with instillation and without significant systemic concentrations. Thereby, a small payload may be implanted, reducing the risk of systemic effects in the event of device failure. Implanting lidocaine in solid form permits further reducing the size of the device to reduce bladder irritation and patient discomfort. The lidocaine may be delivered without regard to the pH of the urine. In one embodiment, the device may have two payloads of lidocaine that are released at different times. The first payload may be adapted for relatively quick release, while the second payload may be adapted for more continuous release. For example, the first payload may be in liquid form or may be housed in a relatively fast-acting osmotic pump, such as a silicone tube having a relatively thinner wall, while the second payload may be solid form or may be housed in an osmotic pump that experiences an initial delay or induction time before releasing, such as a silicone tube having a relatively thicker wall. Thus, the method may continuously release lidocaine into the bladder during an initial, acute phase and during a maintenance phase. Such a method may compensate for an initial induction time of the device.

The present invention may be further understood with reference to the following non-limiting examples.

Example 1: Diffusion of Drug Through the Wall of a Drug Reservoir

A study was performed to determine the feasibility of delivering drug through the wall of a drug reservoir via diffusion. Devices were formed form silicone tubes having an inner diameter of about 0.060 inches, an outer diameter of 0.076 inches, and a length of about 3 cm. The devices were loaded with solid drug tablets of lidocaine, for a total payload of about 60 mg. Some of the devices included an aperture formed through the tube wall, the aperture having a diameter of 150 µm. These devices were loaded with solid tablets of either lidocaine hydrochloride monohydrate or a combination of lidocaine hydrochloride monohydrate and lidocaine base. Other devices did not include an aperture and were loaded with solid drug tablets of lidocaine base. The devices were tested in vitro in water at about 37° C. Release profile data demonstrated that it is feasible to deliver drug via diffusion through a silicone wall without an aperture. The release rate was relatively zero-order over a period of about four days, tapering off thereafter, with the release rate varying based on the device.

Another study was performed to investigate the feasibility of delivering drug from a device through both a wall of a drug reservoir and from an aperture in the wall of the drug reservoir. Devices were formed form silicone tubes having a length of about 3 cm. The devices were loaded with solid drug tablets of lidocaine base, for a total payload of about 60 mg. Five devices had an inner diameter of about 0.060 inches and an outer diameter of 0.076 inches. The first device had one aperture with a diameter of about 150 µm, the second device had two apertures that each had a diameter of about 360 µm, the third device had thirty apertures that each had a diameter of about 360 µm, the fourth device had sixty apertures that each had a diameter of about 360 µm, and the fifth device had no apertures. A sixth device had an inner diameter of about 0.062 inches, an outer diameter of 0.095 inches, and no apertures. The devices were tested in vitro in water at about 37° C. Release profile data showed that lidocaine base can be released from a silicone tube without any apertures and that the release rate can be increased by adding apertures to the device.

Example 2: Study of Particle Size Increase of Lidocaine Via Slugging

Another study was performed to determine the feasibility of increasing the particle size of lidocaine hydrochloride monohydrate by slugging. A 7/16" flat beveled die was used for the study. In one case, an attempt was made to slug lidocaine without any added excipient. However, the lidocaine would not fill the die cavity, even after a force feeder was employed. A composition was then formed by blending lidocaine and PVP. The composition included of 97.1% lidocaine and 2.9% PVP by weight. The composition was subjected to a slugging process, which generated granules with an average particle size of about 424 micron. However, a high percentage of the composition was wasted upon sieving. Particularly, when the granules were sieved with a #30 mesh screen, about 52% of the granules passed through the sieve, about 30% of the granules remained above the sieve, and the remainder of the granules were lost to mill waste. This approach is less favored due to the high scrap rate associated with the slugging process, the poor particle size distribution of the slugged composition, difficultly in packing the slugged composition to achieve a suitable packing density for tableting, and issues during tableting such as sticking.

Example 3: Study of Particle Size Increase of Lidocaine Via Roller Compaction

Yet another study was performed to determine the feasibility of increasing the particle size of lidocaine hydrochloride monohydrate by roller compaction. In one case, lidocaine without any added excipient was processed by roller compaction, which generated granules with an average particle size of about 666 micron. When the granules were sieved with a #40 mesh screen, about 28% of the granules passed through the sieve and about 72% of the granules remained above the sieve. A composition was then formed by blending lidocaine and PVP. The composition included 97.1% lidocaine and 2.9% PVP by weight. The composition was subjected to roller compaction, which generated granules with an average particle size of about 776 micron. When the granules were sieved with a #40 mesh screen, about 25% of the granules passed through the sieve and about 75% of the granules remained above the sieve. The granules were more robust and included fewer fines than the granules produced through roller compaction alone. However, the process was inefficient since the granules were subjected to fluid bed granulation in advance of the roller compaction process.

Example 4: Study of Particle Size Increase of Lidocaine Via Fluid Bed Granulation A study was performed to determine the feasibility of increasing the particle size of lidocaine via fluid bed granulation. In each instance, lidocaine hydrochloride monohydrate was granulated in a fluid bed granulator in the presence of a granulating agent, either water or an aqueous solution of 10% PVP. The batch size of the lidocaine and the spray rate for the granulating agent were recorded, along with the run time and the amount of granulated material generated. The results of the study are provided below in Table 1. The results generally indicate that lidocaine is not amenable to fluid bed granulation with water as the granulating agent, as particle size was not increased. However, lidocaine is amenable to fluid bed granulation with an aqueous solution of PVP. The spray rate of the PVP solution should be controlled to ensure proper granulation, and the inlet temperature should be controlled to prevent melting of the lidocaine.

TABLE 1

Results of Lidocaine Fluid Bed Granulation Study

| Active Ingredient Granulating Agent | Batch Size Spray Rate Run Time/Amount | Result |
| --- | --- | --- |
| Lidocaine DI Water | 600 g 10 g/min Not recorded | Granulation was too wet. Particle size was acceptable, but agglomeration and aggregation occurred upon sitting. Try lower spray rate. |

TABLE 1-continued

Results of Lidocaine Fluid Bed Granulation Study

| Active Ingredient Granulating Agent | Batch Size Spray Rate Run Time/Amount | Result |
|---|---|---|
| Lidocaine DI Water | 600 g 4-6 g/min 25 min/120 g | Batch too small; no improvement in particle size, flow, or handling; blocking overnight. Composition was moisture sensitive. Agglomeration and clogging resulted. Try larger batch size, longer run time. |
| Lidocaine DI Water | 1000 g 4.5-6.5 g/min 54.5 min/300 g | No improvement in particle size, flow, or handling; blocking overnight. Try another granulating agent. |
| Lidocaine 10% PVP solution | 1000 g 4-8 g/min 46 min/300 g | Good particle size, flow, and handling. Clogging on inlet screen due to high inlet temperature above melting point of drug Try different spray rate, lower inlet temp. |
| Lidocaine 10% PVP solution | 1000 g 4.5-6.5 g/min 50 min/300 g | Good particle size, flow, and Handling: no re-agglomeration |
| Lidocaine 10% HPC solution | 1000 g 4.5-6.5 g/min 51 min/275 g | Good particle size, flow, and Handling; no re-agglomeration |

Example 5: Study of Direct Compression of Lidocaine Tablets

A study was performed to determine the feasibility of forming a lidocaine tablet by direction compression of a powder or powder blend. Various tablet compositions were tested using a Korsch XL tablet press. A laboratory scale conical mill and a V-blender were also employed in the study. One composition consisted of only lidocaine HCl $H_2O$ (obtain from Spectrum Chemical). Other compositions included a relatively high weight percentage of lidocaine and a relatively low weight percentage of one of several different excipients. Table 2 describes the various tablet compositions, tablet size, and the results of the direct compression process to form the tablets. The results of the study indicate that lidocaine tableting may be facilitated by adding at least some excipient to the tableted composition, such as to reduce the ejection forces, to improve the flowability of the composition, and to reduce residue and sticking within the tableting apparatus.

TABLE 2

Results of Lidocaine Direct Compression Study

| No. | % by Weight Lidocaine | % by Weight Excipient | Tablet Size | Result |
|---|---|---|---|---|
| 1 | 100% Lidocaine | None | Insert | Ejection force exceeded compression force. |
| 2 | 95% Lidocaine | 5% Sodium Benzoate | 0.25 in. | Some residue on die. Some sticking. |
| 3 | 95% Lidocaine | 5% Sodium Acetate | 0.25 in. | Some residue on die. Some sticking. Higher ejection force. |
| 4 | 94.7% Lidocaine | 5.3% Leucine | 0.25 in. | Some residue on table. Lower ejection force. |
| 5 | 92% Lidocaine | 8% PEG 8000 | 0.25 in. | No residue on table. Higher ejection force. |
| 6 | 95% Lidocaine | 5% Poloxamer 407 | 0.25 in. | Poor flow upon holding after blending. |
| 7 | 95% Lidocaine | 5% Poloxamer 188 | 0.25 in. | Poor flow upon holding after blending. |

Example 6: Tableting Lidocaine and Various Excipients

A study was performed to determine the feasibility of tableting lidocaine with various excipients. In each instance, a composition having lidocaine hydrochloride monohydrate, povidone, and PEG 8000 in various amounts was processed into [mini-] tablets on a tablet machine. The results of the study are provided below in Table 3.

TABLE 3

Results of Lidocaine Tableting Study

| No. | Composition | Result |
|---|---|---|
| 1 | Lidocaine (89.34%) Povidone (2.66%) PEG 8000 (8.00%) | Ran for 30 minutes. Stable. No Picking. Good formula. |
| 2 | Lidocaine (92.23%) Povidone (2.77%) Leucine (5.00%) | No sticking. Ejection forces were higher than compression forces. |

TABLE 3-continued

Results of Lidocaine Tableting Study

| No. | Composition | Result |
|-----|-------------|--------|
| 3 | Lidocaine (95.15%) Povidone (2.85%) PEG 8000 (2.00%) | Ran for 15 minutes. No sticking. Some instability in compression forces due to insufficient lubrication. |
| 4 | Lidocaine (89.34%) Povidone (2.66%) PEG 8000 (8.00%) | Ran for 60 minutes without problems. Preferred formula. |
| 5 | Lidocaine (93.20%) Povidone (2.80%) PEG 8000 (4.00%) | Ran for five minutes. No sticking. Some instability in compression forces due to insufficient lubrication. |
| 6 | Lidocaine (91.26%) Povidone (2.746%) PEG 8000 (6.00%) | Ran for 15 minutes. No sticking. Some instability in compression forces due to insufficient lubrication |

Example 7: Tableting Various Drugs without Excipients

Mini-tablets were made from various different drugs. In a first test, mini-tablets were made from lidocaine (base). In a second test, mini-tablets were made from bupivacaine hydrochloride monohydrate. In a third test, mini-tablets were made from mepivacaine hydrochloride. In a fourth test, mini-tablets were made from oxybutynin hydrochloride. In a fifth test, mini-tablets were made from oxybutynin base. Each tableting test produced mini-tablets successfully. The mini-tablets had a diameter of about 1.5 mm and a length of about 2 mm. No excipients were added to any of the tableted compositions.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. An intravesical drug delivery device comprising:
a device body comprising (i) a drug reservoir tube that defines a drug reservoir lumen, and (ii) a retention frame tube that defines a retention frame lumen;
a plurality of tablets which comprise a drug, the tablets positioned in the drug reservoir lumen; and
a retention frame positioned in the retention frame lumen, wherein the drug tablets are uniform in size and shape and tall enough to retain their orientation once loaded in the drug reservoir lumen, but short enough to provide enough interstices so that the device can flex or move along its length.

2. The intravesical drug delivery device of claim 1, wherein the drug reservoir tube and the retention frame tube are longitudinally aligned and coupled together along their lengths.

3. The intravesical drug delivery device of claim 2, wherein the drug reservoir tube and retention frame tube are formed together of at least one elastomeric material in an extrusion or molding process.

4. The intravesical drug delivery device of claim 1, wherein the drug reservoir tube comprises an aperture in a sidewall of the drug reservoir tube, the aperture being configured to release the drug following at least partial solubilization of the plurality of the drug tablets.

5. The intravesical drug delivery device of claim 4, wherein the aperture is located on a side of the drug reservoir tube that opposes a side on which the retention frame tube is located.

6. The intravesical drug delivery device of claim 1, wherein the device body and the retention frame are elastically deformable together between a relatively lower profile shape for intravesical insertion through a patient's urethra and a relatively higher profile coiled shape for retention of the device within the patient's bladder, the relatively higher profile shape comprising an overlapping coiled shape, wherein interstices formed between any two adjacent drug tablets permit deformation of the device body when the reservoir lumen is filled the plurality of the drug tablets.

7. The intravesical drug delivery device of claim 1, wherein the retention frame comprises a superelastic alloy wire biased into a coiled shape.

8. The intravesical drug delivery device of claim 1, wherein the drug delivery tube comprises a sidewall configured to permit water to diffuse into the drug reservoir lumen when the device is deployed in a patient's bladder.

9. The intravesical drug delivery device of claim 8, wherein the sidewall comprises an aperture configured to release the drug by osmotic pressure following at least partial solubilization of the plurality of the drug tablets.

10. The intravesical drug delivery device of claim 1, wherein each of the plurality of tablets has a diameter from 1.0 mm to 3.2 mm and a length from 1.7 mm to 4.8 mm.

11. An intravesical drug delivery device comprising:
a device body comprising (i) a drug reservoir tube that defines a drug reservoir lumen, and (ii) a retention frame tube that defines a retention frame lumen;
a plurality of tablets which comprise a drug, the tablets positioned in the drug reservoir lumen; and
a retention frame positioned in the retention frame lumen, wherein each of the plurality of tablets has a diameter from 1.0 mm to 3.2 mm and a length from 1.7 mm to 4.8 mm.

12. The intravesical drug delivery device of claim 11, wherein each drug tablet has an aspect ratio of height:width that is greater than 1:1.

13. The intravesical drug delivery device of claim 11, wherein the drug reservoir tube and the retention frame tube are longitudinally aligned and coupled together along their lengths.

14. The intravesical drug delivery device of claim 13, wherein the drug reservoir tube and retention frame tube are formed together of at least one elastomeric material in an extrusion or molding process.

15. The intravesical drug delivery device of claim 14, wherein the drug reservoir tube comprises an aperture in a sidewall of the drug reservoir tube, the aperture being configured to release the drug following at least partial solubilization of the plurality of the drug tablets.

16. The intravesical drug delivery device of claim 15, wherein the aperture is located on a side of the drug reservoir tube that opposes a side on which the retention frame tube is located.

17. The intravesical drug delivery device of claim 16, wherein the device body and the retention frame are elastically deformable together between a relatively lower profile shape for instravesical insertion through a patient's urethra and a relatively higher profile coiled shape for retention of the device within the patient's bladder, the relatively higher profile shape comprising an overlapping coiled shape, wherein interstices formed between any two adjacent drug tablets permit deformation of the device body when the reservoir lumen is filled the plurality of the drug tablets.

18. An intravesical drug delivery device comprising:
a device body comprising (i) a drug reservoir tube that defines a drug reservoir lumen, and (ii) a retention frame tube that defines a retention frame lumen;
a plurality of tablets which comprise a drug, the tablets positioned in the drug reservoir lumen; and
a retention frame positioned in the retention frame lumen,
wherein the drug reservoir tube comprises an aperture in a sidewall of the drug reservoir tube, the aperture being configured to release the drug following at least partial solubilization of the plurality of the drug tablets, and
wherein the aperture is located on a side of the drug reservoir tube that opposes a side on which the retention frame tube is located.

19. The intravesical drug delivery device of claim 18, wherein the drug reservoir tube and the retention frame tube are longitudinally aligned and coupled together along their lengths.

20. The intravesical drug delivery device of claim 19, wherein the drug reservoir tube and retention frame tube are formed together of at least one elastomeric material in an extrusion or molding process.

21. The intravesical drug delivery device of claim 18, wherein the drug tablets are uniform in size and shape and tall enough to retain their orientation once loaded in the drug reservoir lumen, but short enough to provide enough interstices so that the device can flex or move along its length.

* * * * *